(12) United States Patent
Gusso et al.

(10) Patent No.: US 11,786,157 B2
(45) Date of Patent: Oct. 17, 2023

(54) METHOD FOR THE AUTOMATIC EXECUTION OF A STATIC DYNAMIC PERSONALITY TEST OF A PERSON

(71) Applicant: Squadra Internazionale Di Scienze Moderne (Sism) Onlus, San Casciano in Val di Pesa (IT)

(72) Inventors: Claudia Gusso, San Casciano Val di Pesa (IT); Raffaello Gusso, Florence (IT)

(73) Assignee: Squadra Internazionale Di Scienze Moderne (Sism) Onlus, San Casciano in Val di Pesa (IT)

( * ) Notice: Subject to any disclaimer, the term of this patent is extended or adjusted under 35 U.S.C. 154(b) by 458 days.

(21) Appl. No.: 17/266,280

(22) PCT Filed: Jul. 31, 2019

(86) PCT No.: PCT/IB2019/056552
§ 371 (c)(1),
(2) Date: Feb. 5, 2021

(87) PCT Pub. No.: WO2020/031030
PCT Pub. Date: Feb. 13, 2020

(65) Prior Publication Data
US 2021/0312168 A1    Oct. 7, 2021

(30) Foreign Application Priority Data

Aug. 6, 2018  (IT) .......................... 102018000007778
Jan. 11, 2019  (IT) .......................... 102019000000517

(51) Int. Cl.
G06K 9/00      (2022.01)
A61B 5/16     (2006.01)
G06N 7/00     (2023.01)
G06V 40/20    (2022.01)
G06F 18/213   (2023.01)

(52) U.S. Cl.
CPC .............. *A61B 5/16* (2013.01); *G06F 18/213* (2023.01); *G06N 7/00* (2013.01); *G06V 40/20* (2022.01)

(58) Field of Classification Search
CPC ...................................................... G06V 40/20
See application file for complete search history.

(56) References Cited

U.S. PATENT DOCUMENTS 10,282,914 B1 *  5/2019  Tran ................... G06Q 30/0643
2016/0223439 A1 *  8/2016  Asher .................... G01N 21/01
(Continued)

OTHER PUBLICATIONS

Bertol, Daniela: "Being Vitruvian in the movement infrastructure", Symmetry: Culture and Science, vol. 27, No. 4, Jan. 1, 2016, pp. 425-430, XP002796154, p. 427, line 4—p. 428, line 3 p. 429, line 14—p. 430, line 5; figures 3,5—ISR for PCT/IB2019/056552.

*Primary Examiner* — Hadi Akhavannik
(74) *Attorney, Agent, or Firm* — The Webb Law Firm

(57) ABSTRACT

A method for the automatic execution of a Static Dynamic Personality Test (TPSD) of a person, the method involving use of a cubic-spherical container obtained by merging concentrically a cube and a sphere. The method includes taking images of the person and overlapping the cubic-spherical container to the images, and measuring static-dynamic positions of the person as depicted in the images with respect to the cubic-spherical container.

17 Claims, 13 Drawing Sheets

(56) References Cited

U.S. PATENT DOCUMENTS

2017/0270709 A1\* 9/2017 Tran .................... A43B 13/183
2018/0008196 A1 1/2018 Connor
2018/0253906 A1\* 9/2018 Tran ........................ A43B 3/34

\* cited by examiner

Fig.2: Table    Simple and Combined Chromatic Dimensions (Fig1)

| Combined Dimensions | Cod. | Colore Code Color | Volume Dominance | Line Dominance |
|---|---|---|---|---|
| Outward Inward | 0 | White B<br>Gray GB | | |
| Inward 1W (Simple)<br>Backward+Z  Upward-Y  Leftward-X | 1i | Dark Red ROS<br>Light Red ROC | Cubic | Rectilinear |
| Inward1W<br>Forward-Z Downward+Y Rightward+X | 1ii | Dark Red ROS<br>Light Red ROC | Cubic | Rectilinear |
| Backward + Z (Simple)<br>Inward1W Downward+Y Rightward+X | 2i | Dark Brown MAS | Cubic | Rectilinear |
| Backward + Z<br>Outward2W  Upward-Y   Leftward-X | 2e | Light Brown MAC | Cubic | Rectilinear |
| Downward + Y (Simple)<br>Inward1W  Backward+Z  Leftward-X | 8i | Dark Orange ARS | Cubic | Rectilinear |
| Downward + Y<br>Outward2W  Forward-Z  Rightward+X | 8e | Light Orange ARC | Cubic | Rectilinear |
| Rightward + X (Simple)<br>Inward1W    Forward-Z    Upward-Y | 7i | Dark Green VES | Cubic | Rectilinear |
| Rightward + X<br>Outward2WBackward+ZDownward+Y | 7e | Light Green VEC | Spherical | Curvilinear |
| Leftward - X (Simple)<br>Inward1W    Forward-Z    Upward-Y | 4i | Dark Blue BLS | Spherical | Curvilinear |
| Leftward - X<br>Outward2WBackward+ZDownward+Y | 4e | Light Blue BLC | Spherical | Curvilinear |
| Upward - Y (Simple)<br>Inward1W  Backward+Z Rightward+X | 3i | Dark Azure AZS | Spherical | Curvilinear |
| Upward - Y<br>Outwadr2W   Forward-Z    Leftward-X | 3e | Light Azure AZC | Spherical | Curvilinear |
| Forward - Z (Simple)<br>Inward1W   Downward+Y   Leftward-X | 6i | Dark Violet VIS | Spherical | Curvilinear |
| Forward - Z<br>Outward2W   Upward-Y  Rightward+X | 6e | Light Violet VIC | Cubic | Rectilinear |
| Outward 2W (Simple)<br>Forward-Z  Downward+Y  Leftward-X | 5e | Dark Yellow GIS<br>Light Yellow GIC | Spherical | Curvilinear |
| Outward 2W<br>Backward+Z   Upward-Y Rightward+X | 5ee | Dark Yellow GIS<br>Light Yellow GIC | Spherical | Curvilinear |
| Inward Outward | 9 | Black N<br>Gray Black GN | | |

Fig.5 FLOW CHART: "STRUCTURE OF WORK-BOOK"
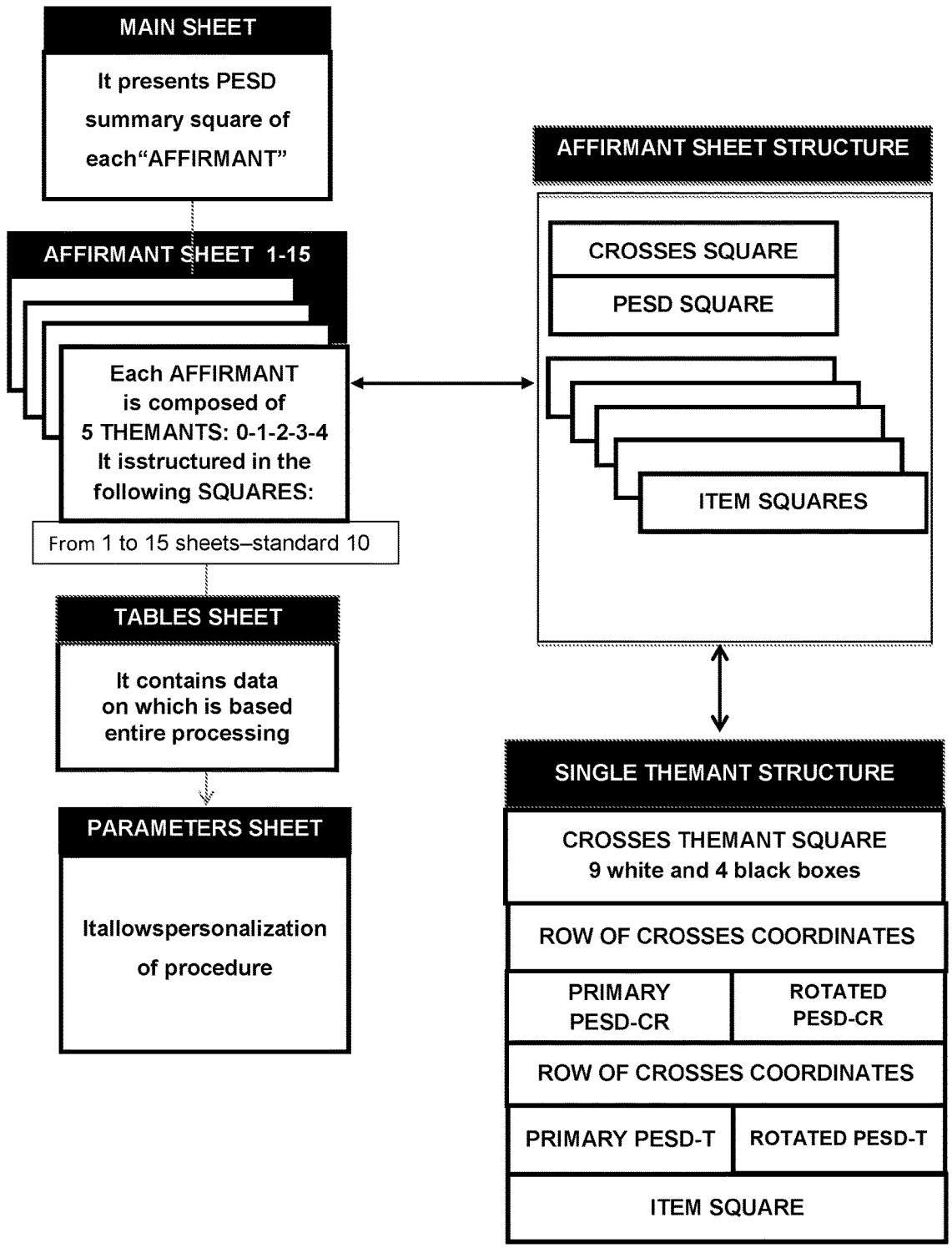

Fig. 6

FLOW CHART:  "SIMBOLOGY and VOCABOLARY"

1 BLOCK START / END Example

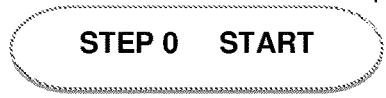
STEP 0   START

**4 BLOCK
FOR AUTOMATIC PROCESSING**

PREPARE SHEETS "AFFIRMANT"

2 BLOCK ITERATION
REPEAT
FOR EACH ELEMENT OF A LIST
R = REPEAT   F = LIST END
Example

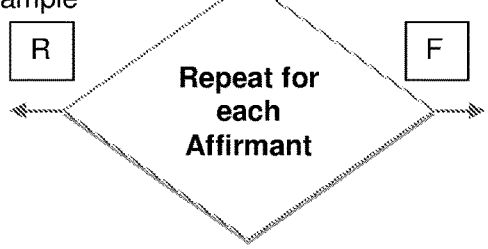
R — Repeat for each Affirmant — F

5 BLOCK FOR ELABORATION WITH INTERVENT OF THE OPERATOR
Example

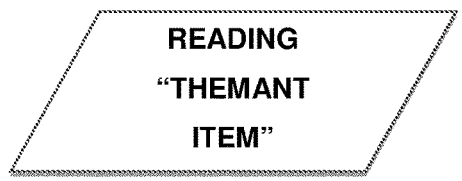
Use STANDARD LIST "Affirmant"

3 BLOCK DICOTOMIC CHOICE
N= No   S= Yes   Example

N — Standard List? — S

6 BLOCK DATA AND RESULTS (OPERATION I/O)   Example

READING "THEMANT ITEM"

ABREVIATION LEGEND
PUNTO CR = Crosses Point
PESD-T = Themant PESD
PESD-A = Affirmative PESD THEMANT: specific theme
AFFIRMANT: global theme
ITEM: meaningful word
CROSS POINT: chosen point
PESD: Static Dynamic Equilibrium Point
INTENSE: Dimension intensity
EXTENSE: Dimension extension
DIMENSION: misura psicofisica

7 BLOCK FOR MANUAL PROCESSING OR EXTERNAL TO TPSD BOOK EXCEL

INTERPRETAZIONE AFFERMANTE

TPSD'18 - MAIN

| N | AFFIRMANT | CROSSES COORDINATES | | | PESD COORDINATES | | | | |
|---|---|---|---|---|---|---|---|---|---|
| | | x | y | Color | x | y | z | w | Color* |
| 0 | DYNAMICS | 1,6 | -0,5 | AZS2 | 1,48 | -0,44 | 0,96 | 0,96 | AZS2 |
| 1 | E-PSYCHE | 0,5 | -1,0 | VES1 | 0,58 | -1 | -0,79 | 0,79 | VES1 |
| 2 | A-PHYSIQUE | -0,6 | -2,4 | BLS2 | -0,54 | -2,22 | -1,38 | 1,38 | BLS2 |
| 3 | HUMAN | 0,3 | -0,4 | VES1 | 0,3 | -0,42 | -0,36 | 0,36 | VES1 |
| 4 | CONSCIENCE | -0,6 | -2,4 | BLS2 | -0,62 | -2,3 | -1,46 | 1,46 | BLS2 |
| 5 | LUMINOUS-PHYSICS | 0,0 | -1,2 | BLS1 | -0,04 | -1,12 | -0,58 | 0,58 | BLS1 |
| 6 | TIME-SPACE | -0,6 | -1,2 | BLS1 | -0,6 | -1,18 | -0,89 | 0,89 | BLS1 |
| 7 | VEGETAL-ANIMAL | -0,8 | -1,7 | BLS2 | -0,8 | -1,58 | -1,19 | 1,19 | BLS2 |
| 8 | INSTRUMENTAL | -1,1 | -1,6 | BLS2 | -1,06 | -1,42 | -1,24 | 1,24 | BLS2 |
| 9 | GAME | -1,7 | -0,4 | ROC2 | -1,84 | -0,38 | 1,11 | 1,11 | ROC2 |
| | CENTRAL PESD | -0,3 | -1,3 | BLS2 | -0,31 | -1,21 | -0,76 | 0,76 | BLS2 |
| | | x | y | m(x,y) | x | y | z | w | m(x,y,z,w) | m(x,y) = Central CR PESD average
m(x,y,z,w) = Central PESD coordinates average
* = Colors Table

| A1 | TABLES |
| A2 | PARAMETERS |

Fig. 7

Fig.8   FLOW-CHART:   "PHOTOGRAMS TREATMENT"
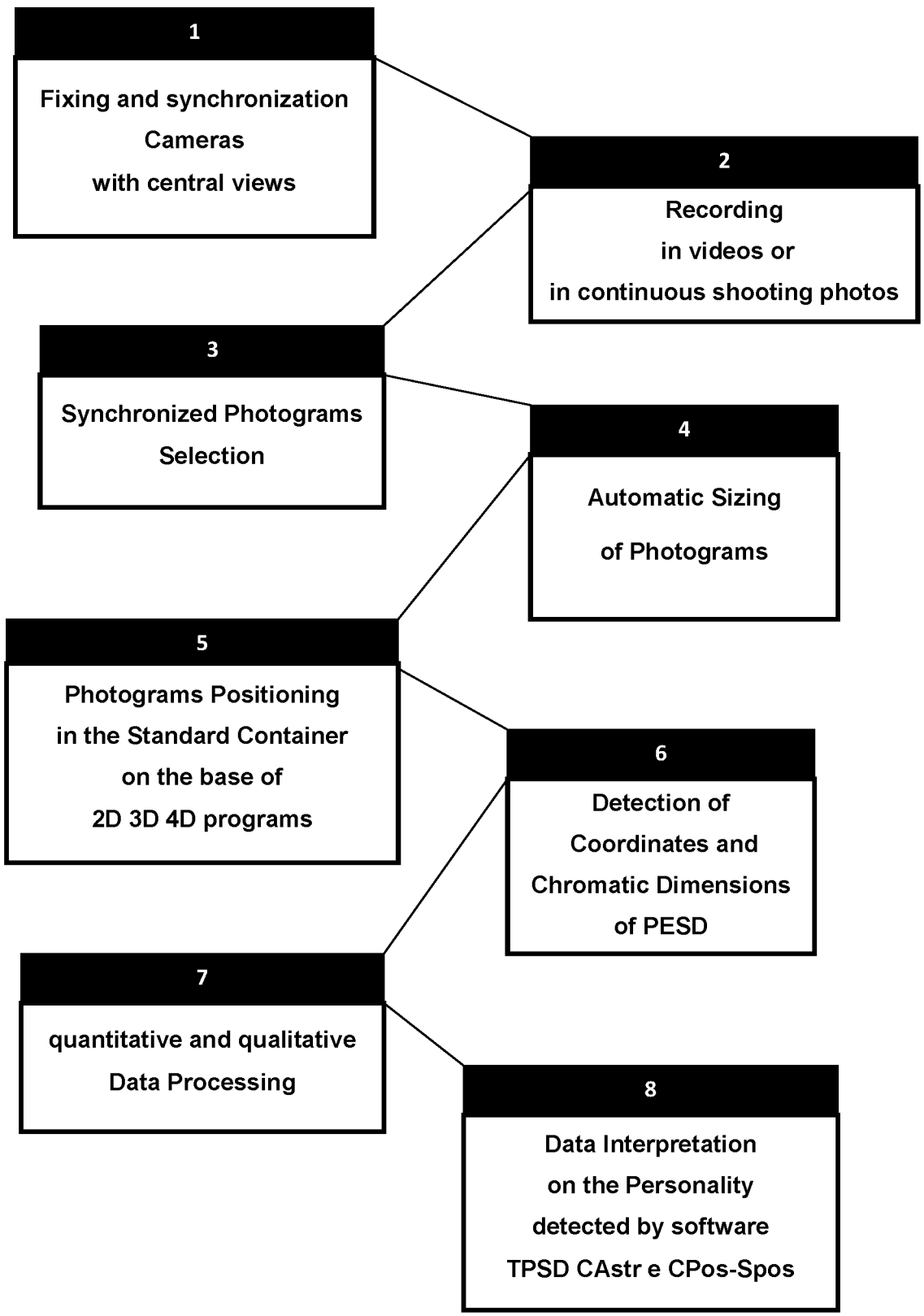

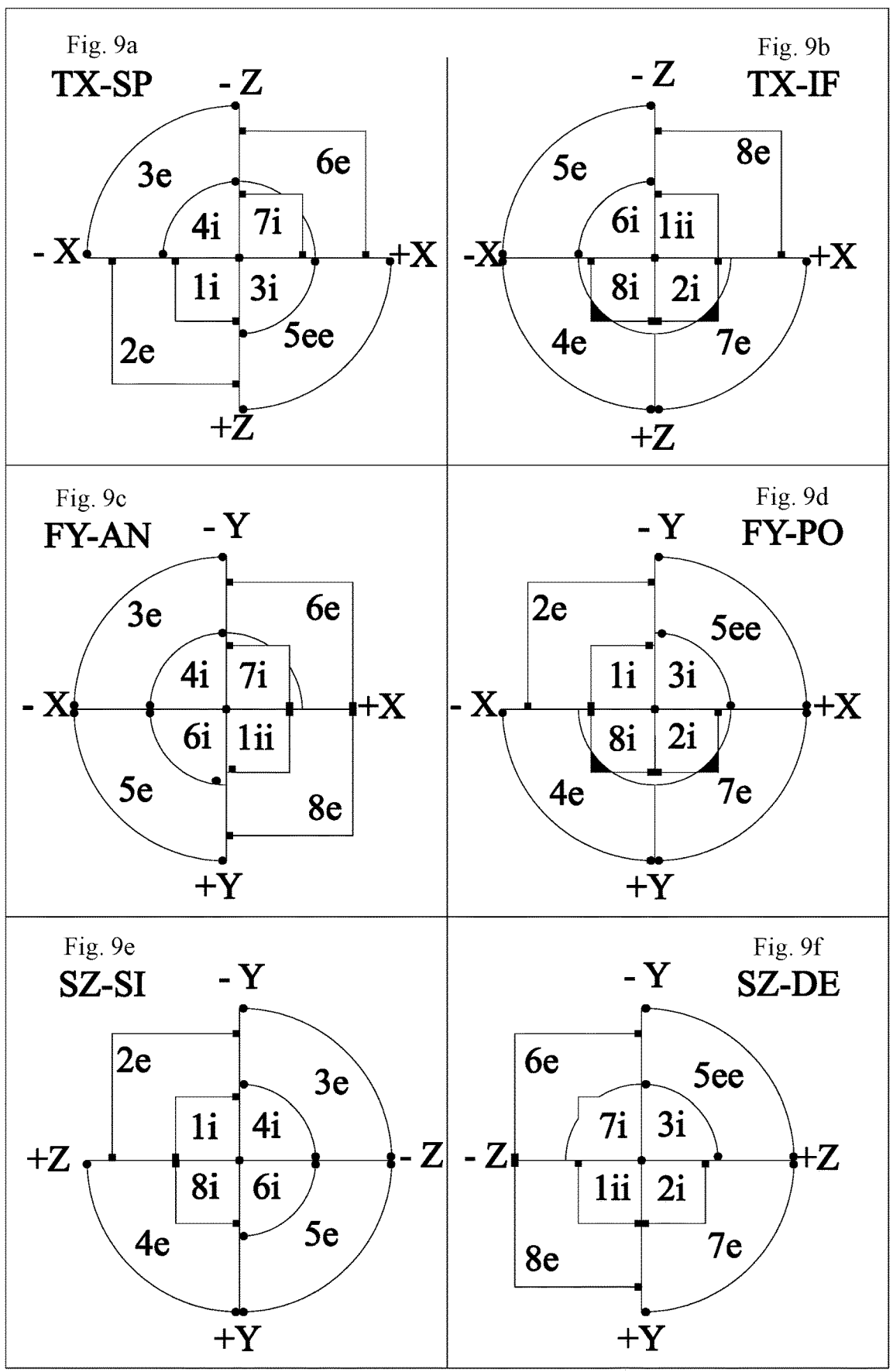

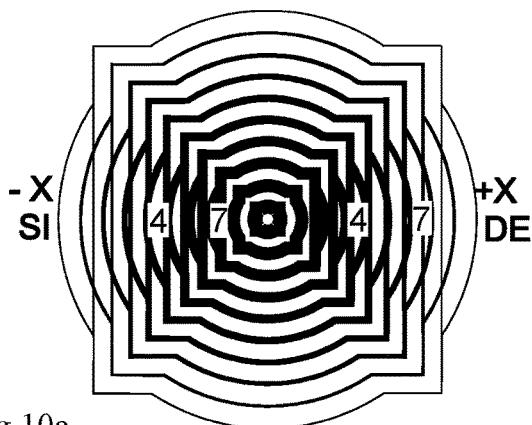
Fig.10a
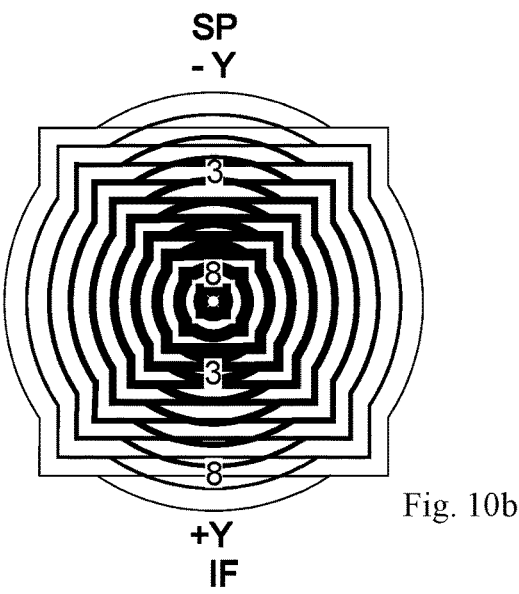
Fig. 10b
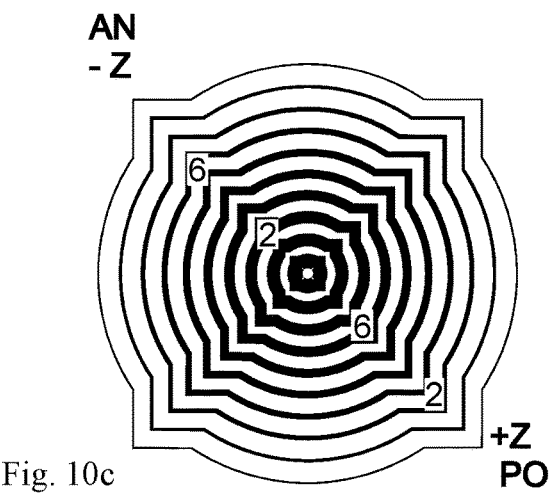
Fig. 10c
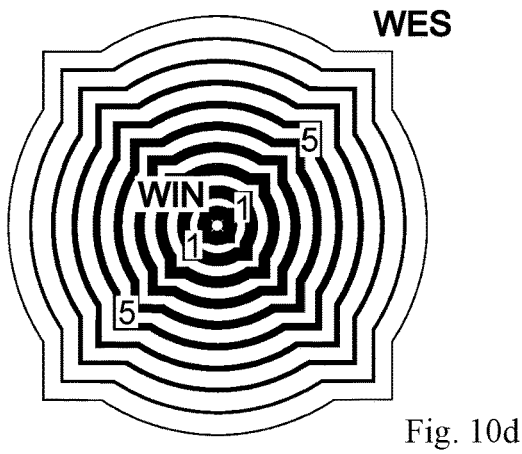
Fig. 10d
Fig. 10e
Fig. 10f
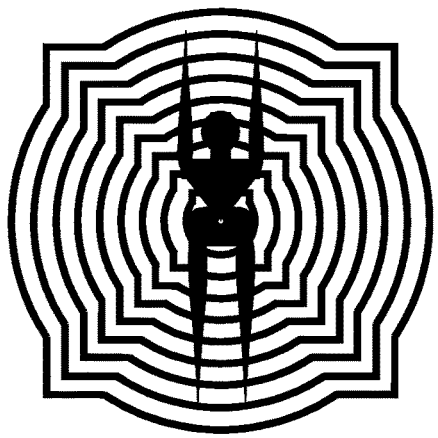
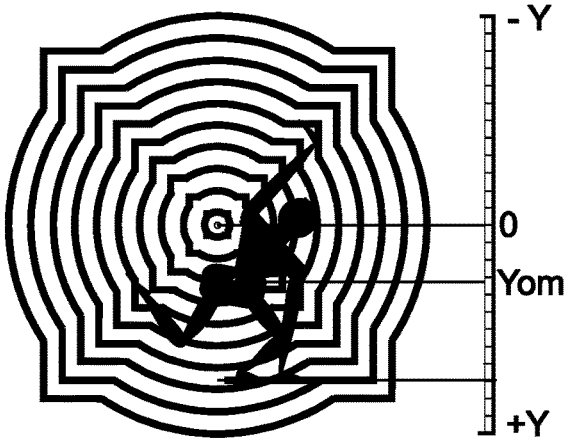

Fig. 11a
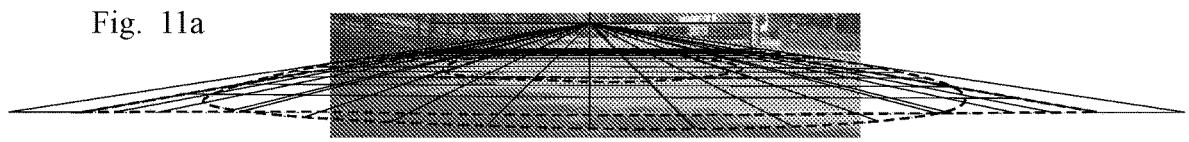
Fig. 11b
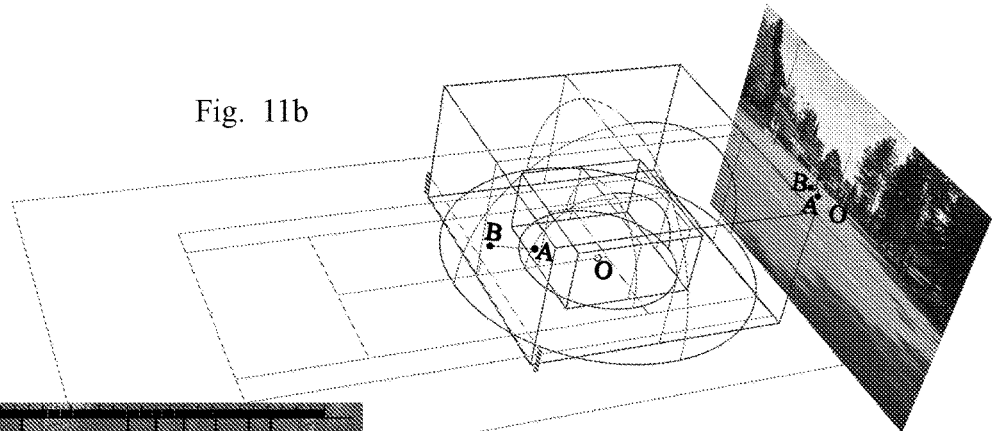
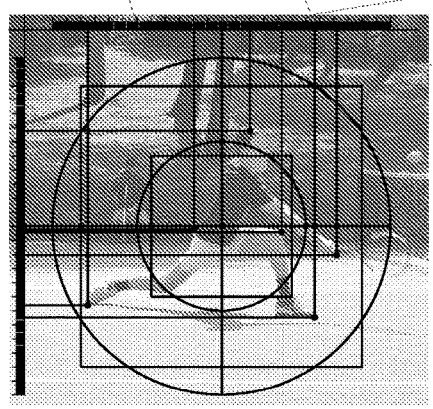
Fig. 11c
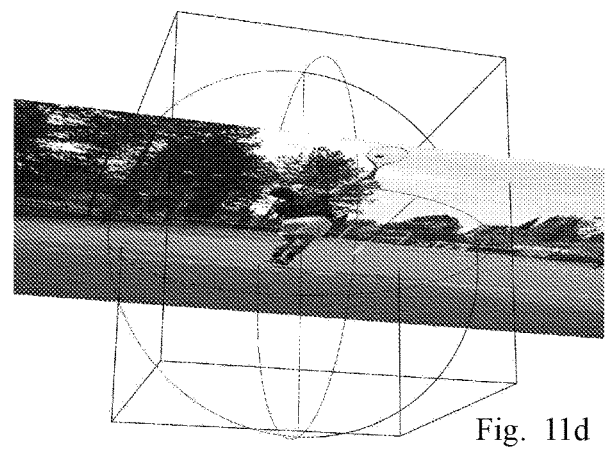
Fig. 11d
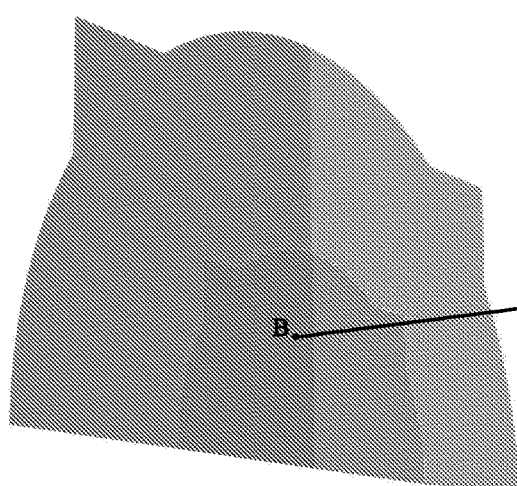
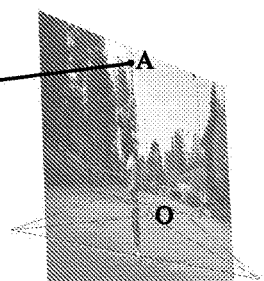
Fig. 11e

METHOD FOR THE AUTOMATIC EXECUTION OF A STATIC DYNAMIC PERSONALITY TEST OF A PERSON

CROSS-REFERENCE TO RELATED APPLICATIONS

This application is the United States national phase of International Application No. PCT/IB2019/056552 filed Jul. 31, 2019, and claims priority to Italian Patent Application Nos. 102018000007778 filed Aug. 6, 2018 and 102019000000517 filed Jan. 11, 2019, the disclosures of which are hereby incorporated by reference in their entirety.

BACKGROUND OF THE INVENTION

Field of the Invention

The present invention relates to a method for performing measurements of psychophysical variables using a Standard Model or Standard Container or Standard Reference System.

In particular, the invention relates to a method for the automatic execution of a static-dynamic personality test (TPSD) of a person.

Description of Related Art

It is desirable to find objective reference systems for the measurement of static-dynamic manifestations of a body inserted in a space, namely the measurement of the static position or of a dynamic movement of that body. The spaces in which the events to be measured occur can be called "situational environments", namely environments in which a wide variety of static-dynamic manifestations are observed.

SUMMARY OF THE INVENTION

It is an object of the present invention to provide a method for the automatic execution of a dynamic static personality test, using reference volumes that determine characteristics suitable for carrying out measurements in objective conditions.

The above and other objects are achieved by a method for the automatic execution of a Static Dynamic Personality Test (TPSD) of a person, comprising the steps of
  prearrangement of a cubic-spherical container obtained by merging concentrically a cube and a sphere, wherein the ratio between half edge of the cube and the radius of the sphere is 5/6, in such a way that the cube and the sphere intersect each other;
  providing a model algorithm comprising predetermined tables, said tables associating combinations of positions of said cubic-spherical container to predetermined test categories, wherein said combinations of positions are determined according to a set of three measurements in an orthogonal XYZ system with parallel directions to edges of said cube, and a fourth measurement W according to a radial direction from the center of said container;
  carrying out on said cubic-spherical container steps selected among:
    physical steps comprising:
      taking images of the person, overlapping said cubic-spherical container to said images, and measuring static-dynamic positions of said person as depicted in said images with respect to said cubic-spherical container, obtaining a plurality of quantitative and qualitative position-displacement measurements of physical Static Dynamic Equilibrium Points (PESDs) of said person, and then automatically correlating of said physical PESDs to said tables of said model algorithm, obtaining a physical Static Dynamic Personality Test result;
    psychic steps comprising:
      projecting said cubic-spherical container on a plane, obtaining a projected plane container, selecting by said person a plurality of psychic Static Dynamic Equilibrium Points (PESDs), and measuring the position of said psychic Static Dynamic Equilibrium Points (PESDs) with respect to said projected plane container, obtaining a plurality of quantitative and qualitative measurements of psychic Static Dynamic Equilibrium Points (PESDs) of said person, and then automatically correlating said psychic PESDs to said model algorithm, obtaining a psychic Static Dynamic Personality Test result;
    a combination thereof obtaining a physical-psychic Static Dynamic Personality Test result.

This method can be considered original and innovative with respect to the known techniques, for the following purposes and particularities:
  a unique model algorithm, hereinafter called also Standard Model is used as a sole reference to make measurements on Personality Dimensions, both for physical variables and for psychic variables;
  the Standard Model provides a dimensional arrangement representing the structure of the body schema and the psychophysical system of a universal human being, therefore considered an Objective Reference System for measurements of physical variables of position/displacement in space and of psychic variables of a person subject;
  possibility of using a specifically designed TPSD Software (Static Dynamic Personality Test) can be made that is based on the Standard Model, in order to include measurement ratios related to psychic variables extracted from the projected plane container, hereinafter called also Abstract Container, and physical variables extracted from the cubic-spherical container, hereinafter called also Position-Displacement Container;
  possibility of using Scientific Categories based on the Standard Model to use measurement ratios related to psychic variables and physical variables:
  possibility of making measurements of movement/position/displacement variables made on images—photos or photograms—produced by cameras or video cameras without the use of markers: the method allows applications in situational environments such as performance halls, sports fields, work environments, internal and external environments. Advantageously, the cubic-spherical container is a Position-Displacement Standard Container (CSPos-Spos) that can be occupied both in position and in displacement by images of said person, or by said person physically or by parts of the body of said person, in a plurality of said PESDs and is configured as a cubic-spherical container with a cube side dimension between 1.00 dm-1000 dm, in particular between 1.00 dm-100.00 dm, and a sphere diameter dimension between 1.20 dm-1200 dm, in particular between 1.2 dm and 120.00 dm, said cube side dimension and sphere diameter dimension compared to real size of said person, of parts of the body of said person or of an environment in which said person is moving.

In a preferred embodiment, the measurements that are carried out in said cubic-spherical container comprise a set of three measurements in an orthogonal XYZ system with parallel directions to edges of said cube, and a fourth measurement W with a radial direction from the center.

Preferably, said steps of execution in said cubic-spherical container of a plurality of measurements and said steps of evaluation of said measurements according to said model algorithm are made by program means referred to said cubic-spherical container are carried out by an Instrumental Technical Plant configured for analysis, measurement, interpretation, evaluation of stability and dynamism of the personality, said Instrumental Technical Plant comprising a TPSD software that sets said Instrumental Technical Plant according to said cubic-spherical container.

Advantageously, the cubic-spherical container has a center and said W Coordinate identifies the PESD with respect to a chromatic density which is maximum at said center and decreases as the distance from said center increases.

In a possible embodiment said chromatic density that measures the W Coordinate of said PESD is identified according to an Intense-Medium Intense-Medium Extense-Extense Ordinal Scale and Interval Scale in intermediate degrees.

In a preferred embodiment, the W Coordinate, is calculated from an Inward Intense to an Outward Extense grade, by executing an Average of said X Y Z Coordinates responsive to a proximity of the PESD to predetermined Median Planes, TZ Transverse, FY Frontal, SZ Sagittal, and a W value is obtained by the resultant of distinct tendencies of each X Y and Z Coordinates to be more or less distant from a value 0 with respect to said Median Planes. In preferred embodiments said PESD can be determined in a way selected among:

in a Spherical Volume dominance where the X Y Z Coordinates define, in quantity and quality, a position and direction in a curved mode, a definition step being provided of a Standard Sphere to which the PESD belongs, the said W Coordinate being calculated as the length of Standard Sphere Radius using the X Y Z Coordinates of the PESD identified in said Spherical Volume;

in a Cubic Volume dominance, wherein the X Y Z Coordinates define, in quantity and quality, a position and direction in straight mode, being foreseen a phase of definition of a Standard Cube to which the PESD belongs, the said W Coordinate being calculated as the length of the segment that joins the PESD to the Center;

in particular, if said PESD has a rectilinear trajectory said Cubic Volume dominance is selected, and if said PESD has a curved trajectory said Spherical Volume dominance is selected.

Advantageously, position-direction ratios and fixed proportion ratios of said PESD are calculated and delimited by concentric and intersected Volumes in Cubic Volume dominance and in Spherical Volume dominance and determined in proportion 5 for the cubic component with respect to half edge of the cube of said cubic spherical container and in proportion 6 for the spherical component with respect to the radius of the sphere of said cubic spherical container.

Preferably, said X Y Z W Coordinates are calculated on the base of the said Cubic Volumes and Spherical Volumes and measured with said proportion ratios, each PESD being represented as two correspondent points called Twin Points, one of cubic components and one of spherical components.

In a possible embodiment, said components are measured according to Standard Cubes and Standard Spheres, according to which to a cube edge 100 and to a sphere diameter 120 the following respectively correspond:

to an integer value 50 Standard Cubes and 50 Standard Spheres to a decimal value 500 Standard Cubes and 500 Standard Spheres to a centesimal value 5000 Standard Cubes and 5000 Standard Spheres.

In preferred embodiments, the step of automatically correlating said PESD to said model algorithm comprises an association of a predetermined color to a predetermined combination of position and direction.

Advantageously, a physical cubical spherical container can be further used in a way that is configured as laboratory for the study of human dynamics (SHD) in which said TPSD measurements are carried out, said physical cubical spherical container having flat and curved walls, pyramidal roof, square and circular floor, water and ground spaces under the floor level, in such a way that static dynamic activities to which quantitative and qualitative measurements can be made.

Further advantages of any of the above embodiments are the following:

possibility of application of the Standard Model on images of position, displacement, movement of person subjects to make measurements referred to Orthogonal Coordinates X Y Z and Oblique Coordinate W (Combined Coordinate);

possibility of use of W or density measurement or fourth measure or fourth coordinate for detecting combination values of orthogonal variables X Y Z;

possibility of use of the Standard Model to measure movement variables of parts of the human body with reference to the center of equilibrium;

possibility of use of the Standard Model to measure position and displacement variables of parts of the body or of the entire human body with reference to the situational environment;

possibility of use of the Cubic-Spherical Standard Model to perform measurements of rectilinear and curvilinear variables;

possibility of use of the Standard Model of Cubic Spherical Container for the arrangement of architectural spaces, in industrial mechanics, reproduced in virtual systems, for modeling commercial products.

Another feature is that the Standard Container can provide eight Chromatic Dimensions and 16 Combined Dimensions as a reference system organized on the combination of volumes within which the method is applied to carry out objective measurements on the static-dynamic of the bodies.

The Standard Container has a rational and fixed structure that maintains the properties of the Standard Model and it is transferable to the different environments, scopes or contexts. Application examples describe the Standard Model applied to Standard Containers in abstract scopes and for the measurement of positions and displacements, useful for practices of the analysis, measurement, interpretation, assessment of stability and variability of psychophysical bodies with use of a TPSD Software (Static Dynamic Personality Test).

Advantageously said association the following colors are used according to the following:

| SIMPLE POSITIONS-DIRECTIONS | SIGN - VALUE | COLOR | NUMBER |
|---|---|---|---|
| Lateral Rightward | positive algebraic sign +X | Green | 7 |
| Lateral Leftward | negative algebraic sign −X | Blue | 4 |
| Inferior Downward | positive algebraic sign +Y | Orange | 8 |
| Superior Upward | negative algebraic sign −Y | Azure | 3 |
| Posterior Backward | positive algebraic sign +Z | Brown | 2 |
| Anterior Forward | negative algebraic sign −Z | Violet | 6 |
| Intense Inward | 1W value | Red | 1 |
| Extense Outward | 2W value | Yellow | 5 |

Preferably, said association of positive or negative Algebraic Signs and orthogonal Positions Directions of said components are determined with reference to the body system of the human being (27) according to the following list:
+X Psychophysical Dominance Lateral Rightward
−X Psychophysical Alternative Lateral Leftward
+Y Psychophysical Gravity Inferior Downward
−Y Psychophysical Antigravity Superior Upward
+Z Psychophysical Pressure Posterior Backward
−Z Psychophysical Advance Anterior Forward
1W Psychophysical In-Tension Intense Inward
2W Psychophysical Dis-Tension Extense Outward Advantageously, in said association the following combined dimensions are used according to the following list:

| Combined Dimensions | Cod. | Colore Code Color | Volume Dominance | Line Dominance |
|---|---|---|---|---|
| Outward Inward | 0 | White B Gray GB | | |
| Inward 1W Backward +Z Upward −Y Leftward −X | 1i | Dark Red ROS Light Red ROC | Cubic | Rectilinear |
| Inward1W Forward −Z Downward +Y Rightward +X | 1ii | Dark Red ROS Light Red ROC | Cubic | Rectilinear |
| Backward +Z Inward1W Downward +Y Rightward +X | 2i | Dark Brown MAS | Cubic | Rectilinear |
| Backward +Z Outward2W Upward −Y Leftward −X | 2e | Light Brown MAC | Cubic | Rectilinear |
| Downward +Y Inward1W Backward +Z Leftward −X | 8i | Dark Orange ARS | Cubic | Rectilinear |
| Downward +Y Outward2W Forward −Z Rightward +X | 8e | Light Orange ARC | Cubic | Rectilinear |
| Rightward +X Inward1W Forward −Z Upward −Y | 7i | Dark Green VES | Cubic | Rectilinear |
| Rightward +X Outward2WBackward +Z Downward +Y | 7e | Light Green VEC | Spherical | Curvilinear |
| Leftward −X Inward1W Forward −Z Upward −Y | 4i | Dark Blue BLS | Spherical | Curvilinear |
| Leftward −X Outward2WBackward +Z Downward +Y | 4e | Light Blue BLC | Spherical | Curvilinear |
| Upward −Y Inward1W Backward +Z Rightward +X | 3i | Dark Azure AZS | Spherical | Curvilinear |
| Upward −Y Outwadr2W Forward −Z Leftward −X | 3e | Light Azure AZC | Spherical | Curvilinear |
| Forward −Z Inward1W Downward +Y Leftward −X | 6i | Dark Violet VIS | Spherical | Curvilinear |
| Forward −Z Outward2W Upward −Y Rightward +X | 6e | Light Violet VIC | Cubic | Rectilinear |
| Outward 2W Forward −Z Downward +Y Leftward −X | 5e | Dark Yellow GIS Light Yellow GIC | Spherical | Curvilinear |
| Outward 2W Backward +Z Upward −Y Rightward +X | 5ee | Dark Yellow GIS Light Yellow GIC | Spherical | Curvilinear |
| Inward Outward | 9 | Black N Gray Black GN | | |

Preferably, said program means, or TPSD Software, assign to each combination of position-direction components qualitative aspects extracted by the cubic/spherical container are selected among: Dynamic, E-psyche, A-physique, Human, Conscience, Luminous-Physics, Time-Space, Vegetal-Animal, Instrumental, Game, and each qualitative aspects is defined as a respective Scientific Category, to each Scientific Category a sequence of Thematic Categories corresponding.

BRIEF DESCRIPTION OF THE DRAWINGS

The invention will be now shown with the description of its exemplary embodiments, exemplifying but not limitative, with reference to the attached drawings, in which like reference characters designate the same or similar parts, throughout the figures of which:

FIGS. 1a and 1b are a schematic representation of a Standard Model according to;

FIG. 2 is a table of simple and combined dimensions of the standard model of FIGS. 1a and 1b;

FIG. 3b is a cross section concentric and intersected cubes spheres of the Cubic-Spherical Standard Container of FIG. 3a;

FIG. 5 shows a Flow Chart: Structure of a Work-Book;

FIG. 6 shows a flow Chart Symbology and Vocabulary;

FIG. 7 shows a Main Sheet of Data detected by a TPSD Software;

FIG. 8 shows a Flow Chart: of Photograms Treatment;

FIGS. 9a-9f depicts Median Plans of the Standard Model according to the invention;

FIGS. 10a-10f shows Chromatic Bands on different plans;

FIGS. 11a-11e show different applications of the method in different respective sports positions;

DESCRIPTION OF THE INVENTION

The following is a detailed description of the drawings.

Figure 1A:
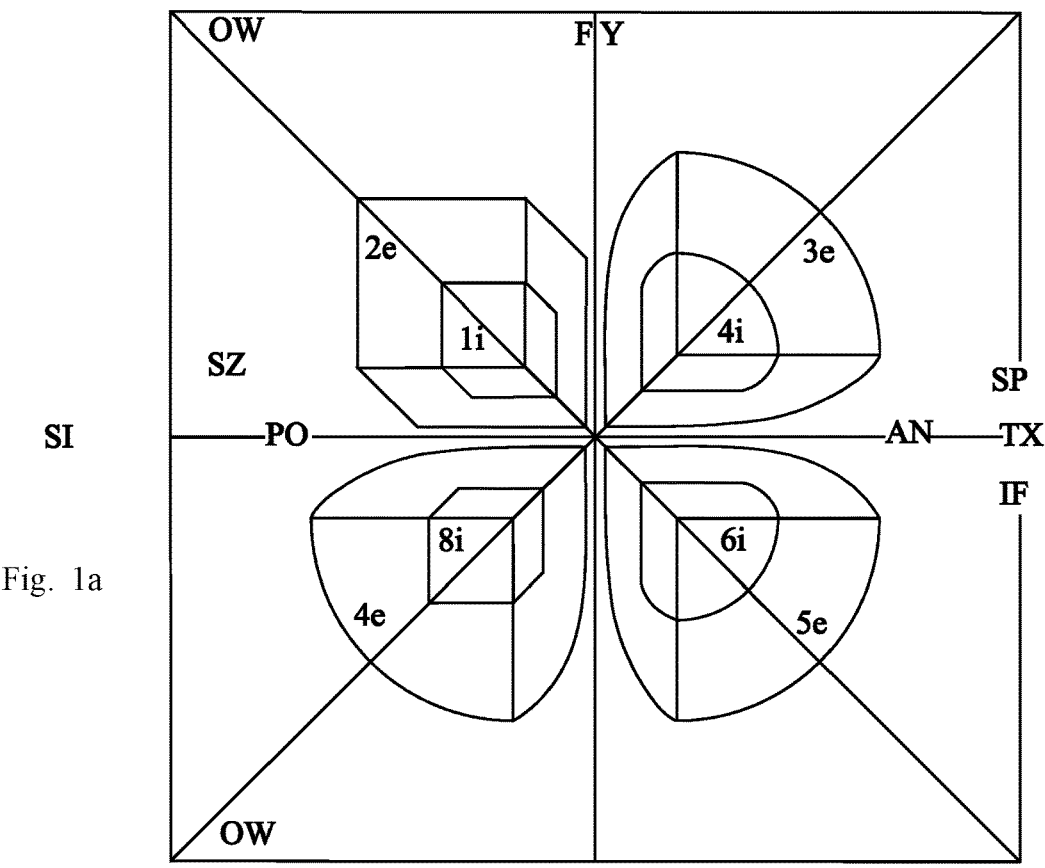
Figure 1B:
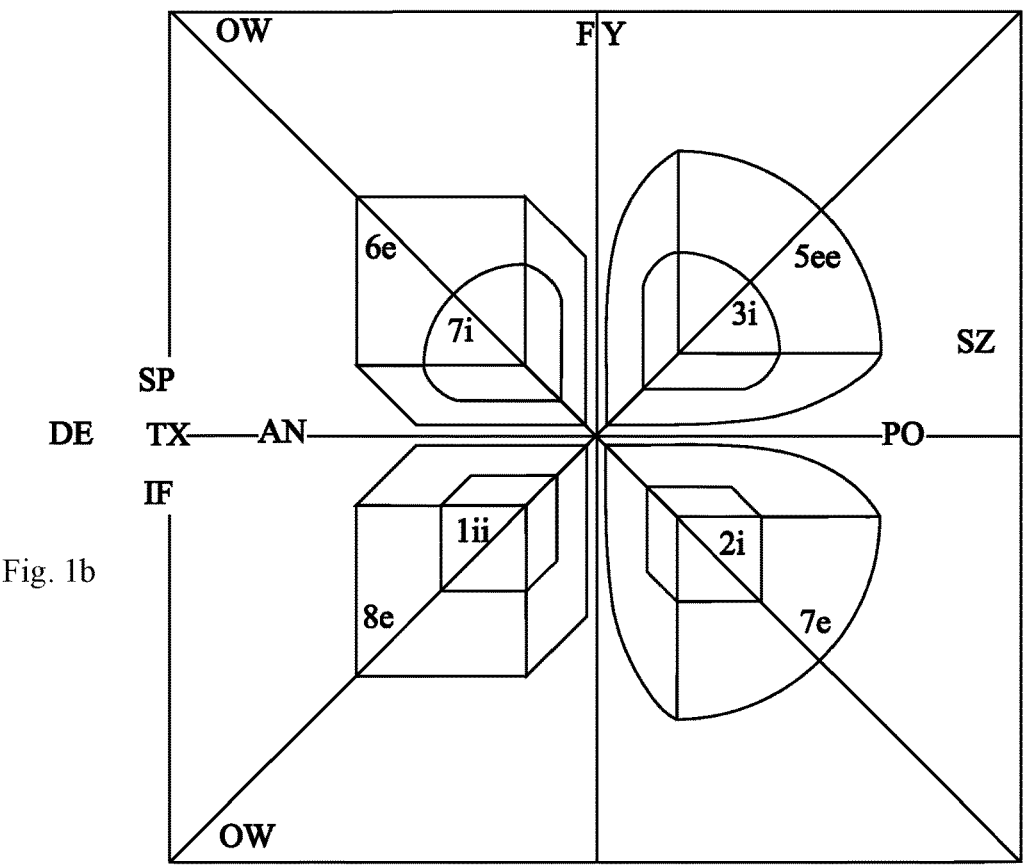

FIG. 1 a: "Standard Model". Sagittal Plan (SZ), Line of Transverse Plan (TX), Line of Frontal Plan (FY), Line of Oblique Plan (OW)

In Space on the Left (SI), of Cubic-Spherical Standard Container, 8 Volumes of Combined Dimension (FIG. 2) are visible:

In Space on the Left (SI) 4 Inward (i) Volumes are placed: 1i; 4i; 6i; 8i.

In Space on the Left (SI) 4 Outward (e) Volumes are placed: 2e; 3e; 5e; 4e.

In Superior Space (SP) 4 Upward Volumes are placed: 1i; 2e; 4i; 3e.

In Inferior Space (IF) 4 Downward Volumes are placed: 8i; 4e; 6i; 5e.

In Posterior Space (PO) 4 Backward Volumes are placed: 1i; 2e; 8i; 4e.

In Anterior Space (AN) 4 Forward Volumes are placed: 4i; 3e; 6i; 5e.

FIG. 1 b: In Space on the Right (DE), 8 Volumes are visible:

In Space on the Right (DE) 4 Inward (i) Volumes are placed: 1ii; 7i; 3i; 2i.

In Space on the Right (DE) 4 Outward (e) Volumes are placed: 8e; 6e; 5ee; 7e

In Superior Space (SP) 4 Upward Volumes are placed: 7i; 6e; 3i; 5ee.

In Inferior Space (IF) 4 Downward Volumes are placed: 1ii; 8e; 2i; 7e.

In Posterior Space (PO) 4 Backward Volumes are placed: 2i; 7e; 3i; 5ee.

In Anterior Space (AN), 4 Forward Volumes are placed: 1ii; 8e; 7i; 6e.

FIG. 2: "Table"—From the left in the 1st column, 16 Combined Dimensions (FIG. 1), or Chromatic Volumes, each linked to 4 PositionsDirections, or Four-Dimensional XYZW; in 2nd column, Positions and Directions Codes of 16 Combined Dimensions with "I" as internal and "e" as external; in 3rd column, Combined Dimension Color and Color Code with internal Dark (S) and external Light (C); in 4th column, Form VolumeDominance in Combined Dimension Space; in 5th column, Form Lines Dominance on the Combined Dimension Plan.

Figure 3F:
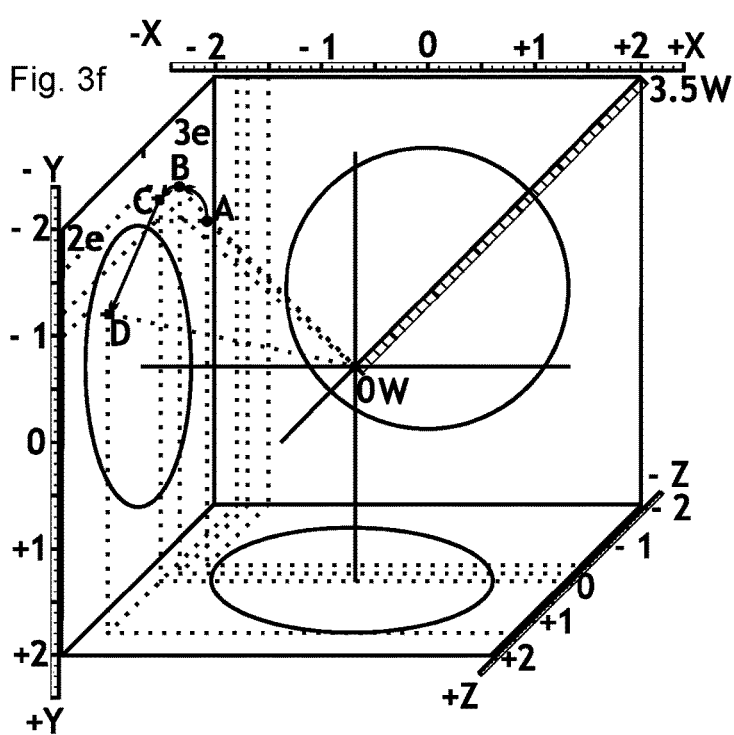
FIG. 3f depicts a 4D Grid with Scales is used to identify X Y Z W Values and the Color Dimension of a Point or a Set of Points.
Figure 3G:
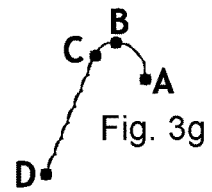
FIG. 3g is a detail of the ABCD tracing in FIG. 3f.
Figure 3A:
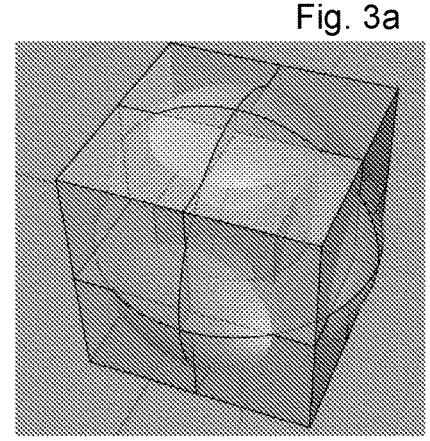
FIG. 3a is a Four-dimensional Image of Cubic-Spherical Standard Container according to the invention.

FIG. 3a: "Four-dimensional Image of Cubic-Spherical Standard Container" (8,11). The margins of the Combined Dimensions Volumes, 1W Internal Cube Sphere and 2W External Cube Sphere, are represented by the visible containers. Therefore, measures of Inward Outward referring to Oblique Plans, are added to orthogonal measures on the Sagittal Frontal Transverse Plans FIG. 3b: "Section concentric and intersected cubes spheres, in Proportion Ratio" (10,12). Points ABC D with squares are referred to Cubes. Points A B C D with circles are referred to Spheres. The Corresponding Points, with equal letter, are called Gemini Points, one of rectilinear measure and one of curvilinear measure. Points are placed on graduated Volume Densities: thick line W Intense Inward, medium thick line W Medium Intense Inward, medium thin line W Medium Extense Outward, thin line W Extense Outward.

Figure 3C:
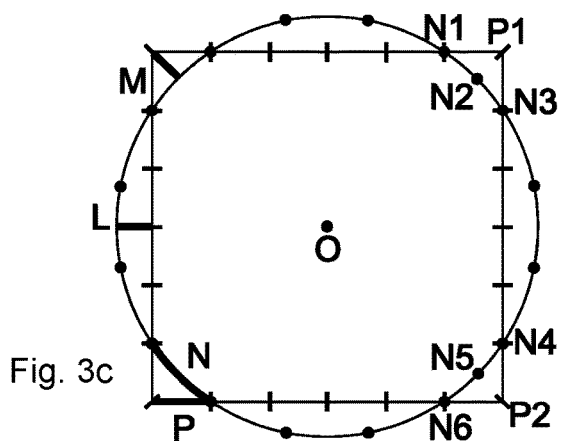
FIG. 3c shows Constance of Distances in the spherical and cubic domain of the Cubic-Spherical Standard Container.

FIG. 3c: "Constance of Distances" (13). L=ML is the segment that joins the vertex of the spherical cap with the midpoint of the subtended side of the cube; M is the segment that joins the vertex of the corner of the cube with the vertex of the subtended spherical cap.

The square cube and circular sphere sections are concentric and with divided perimeters: the rectilinear segment P, between two bars, is repeated 24 times on the perimeter of the square section; the curvilinear segment N, between two circles, is repeated 16 times on the perimeter of the circular section.

Figure 3B:
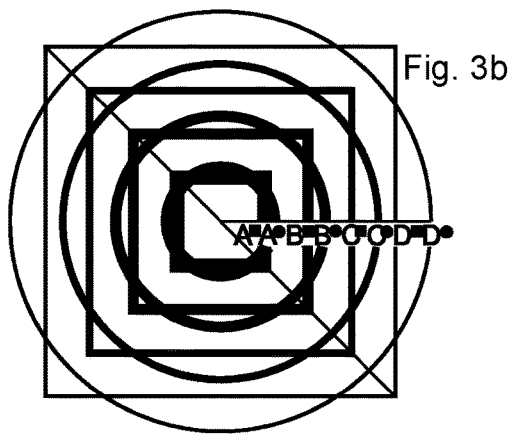
Figure 3D:
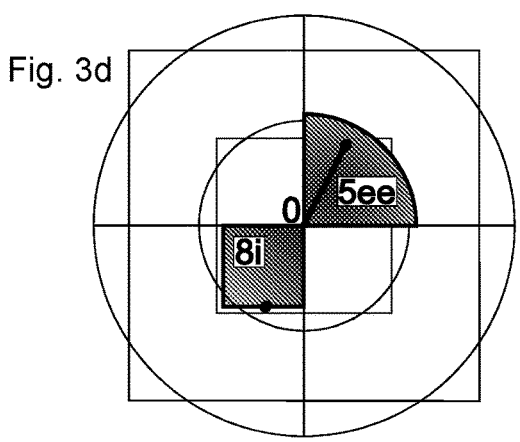
FIG. 3d depicts schematically Points of Static Dynamic equilibrium PESD measured in the Cubic-Spherical Standard Container.

FIG. 3d: "PESD" (14) in Dimension 5ee Dark Yellow Outward Backward Rightward Upward positioned on the proper spherical section as a part of Standard Sphere. The PESD belongs to Spherical Dominance Combined Dimension and to a single Standard Sphere.

The Standard Sphere of the PESD is distant from the center for a Value W calculated as radius or Fourth Coordinate. PESD in Dimension 8i Dark Orange Inward Backward Leftward Downward positioned on the proper cubic section as a part of Standard Cube ( ).

The PESD belongs to Cubic Dominance Combined Dimension and to only one Standard Cube. The Standard Cube is distant from the center for fixed W Values, including the W of the PESD calculated as the Fourth Coordinate.

Figure 3E:
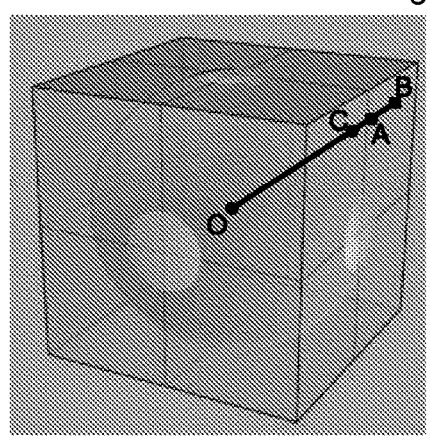
FIG. 3e shows twin points measured in the Cubic-Spherical Standard Container.

FIG. 3e: "Gemini Cubic PESD and Spherical PESD of PESD A" (16).

Spherical PESD A has a Cubic PESD B on the corresponding Standard Cube.

Cubic PESD A has a Spherical PESD C on the corresponding Standard Sphere.

From the center 0, diagonal line W passing through PESDs B A C is traced.

FIG. 3f: "The 4D Grid with Scales" (15) is used to identify X Y Z W Values and the Color Dimension of a Point or a Set of Points. Displacement of PESD A and B in Dimension 3e Light Azure spherical dominance and of PESD C and D in Dimension 2e Light Brown cubic dominance.

FIG. 3g: "Detail of FIG. 3f" (15). For standard ratios, the A B C D tracings can be broken down both as rectilinear and as curvilinear.

Figure 4A:
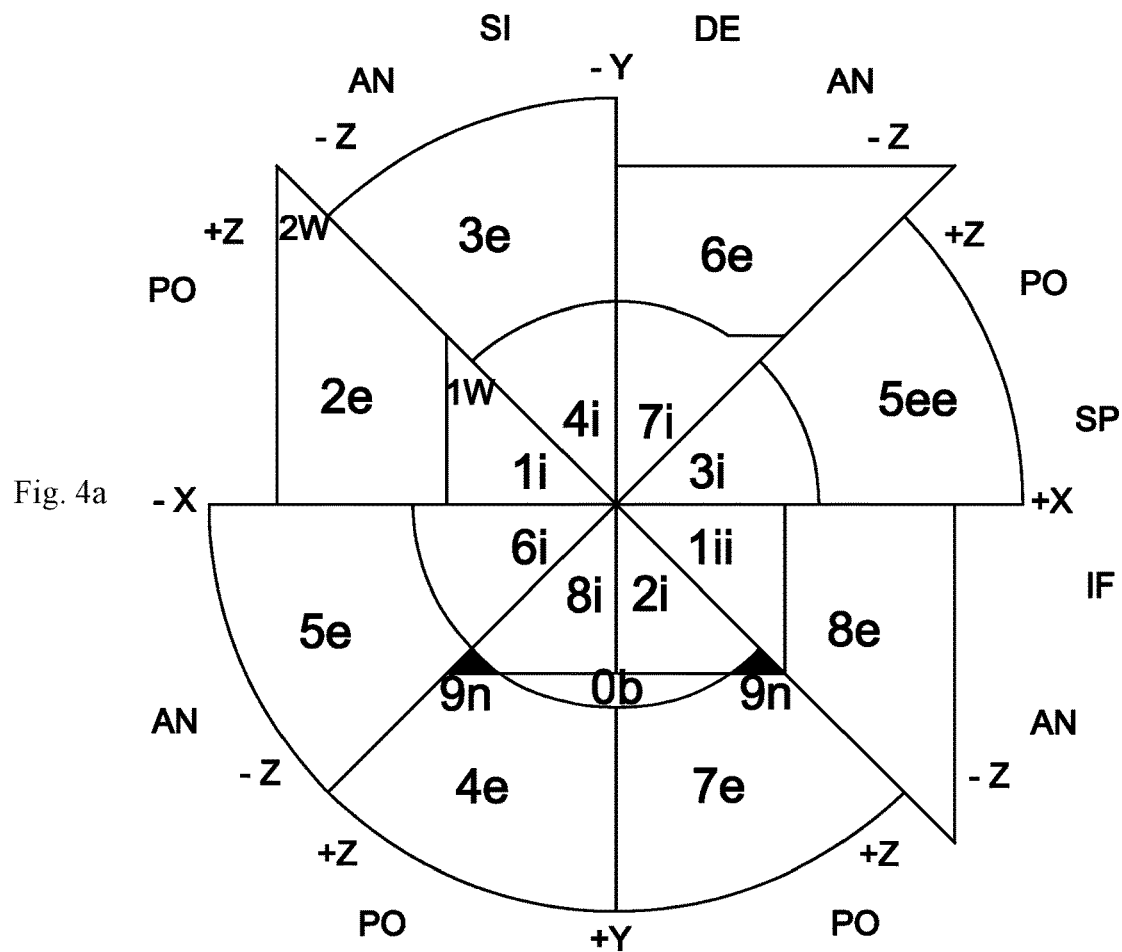
FIG. 4a shows an Abstract Standard Container according to the invention.

FIG. 4a: "Abstract Standard Container". Standard Model is represented on an Abstract Geometric Plan with 16 Combined Dimensions (FIG. 1).

Dimensions, positioned on Right part of the model, are in the right part of Plan.

Dimensions, positioned on Left part of the model, are in the left part of Plan.

Dimensions, positioned on Down part of the model, are in the down part of the Plan.

Dimensions, positioned on Up part of the model, are in the up part of Plan.

Dimensions, positioned on Back part of the model, are below Forward Dimensions, positioned on the same Right or Left or Up or Down part.

Dimensions, positioned on Forward part of the model, are above Backward Dimensions, positioned on the same Right or Left or Up or Down.

Figure 4B:
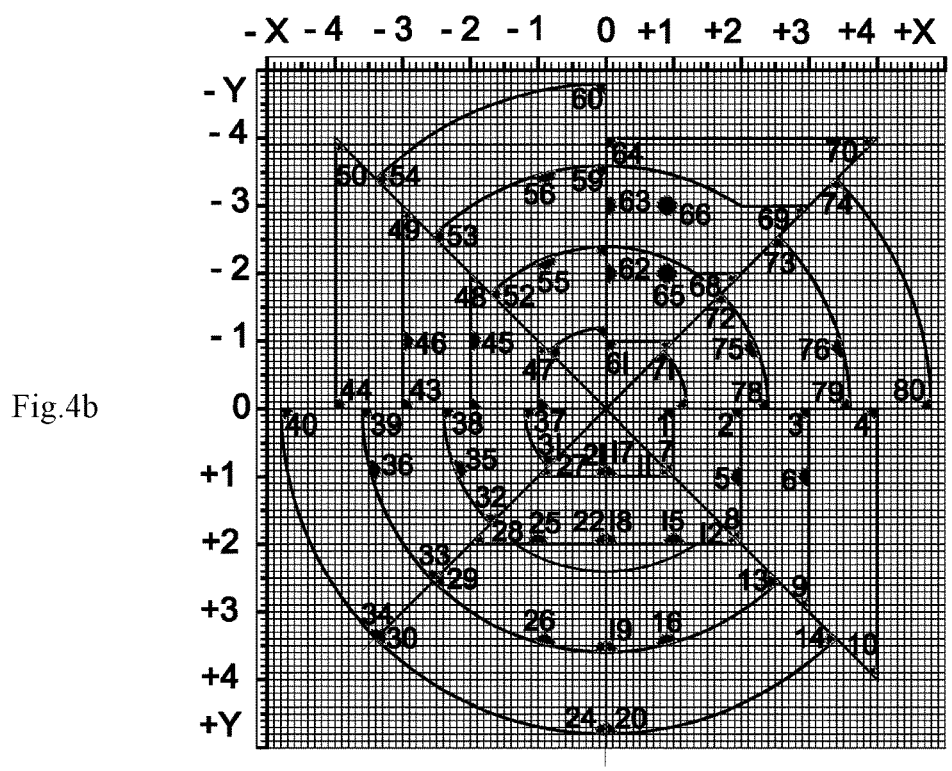
FIG. 4b shows eighty Standard PESDs represented on an Abstract Geometric Plan.

FIG. 4b: "The 80 Standard PESDs" (20) represented on the Abstract Geometric Plan and numbered according to the position in 8 Sectors and 4 Levels. There are 10 Standard PESDs in each Sector. In each Internal or External Level there are 2 Standard PESDs. In each Medium Internal or Medium External level there are 3 Standard PESDs. The Grid, with decimal Scale, identifies the Standard PESD on Original Coordinates X Y. The Derived Coordinates Z and W are calculated by averages of coefficients X Y.

FIG. 5: "Flow Chart: Structure of Work-Book" (23). Structure of TPSD CSAst Software. FIG. 6: "Flow Chart: Symbology and Vocabolary" (22). Symbology of TPSD CSAst Software and specific Vocables used in TPSD.

FIG. 7: "Main Sheet". Data detected by the TPSD Software CSAst on Chromatic Dimensions and Standard PESD of the Person subject. The Blue Dimension is highlighted in greater breadth, related to the data detected by the analysis of dynamics in the tennis court with CSPos-Spos.

FIG. 8: "Flow Chart: Photograms Treatment" (31). Photograms Treatment sequence and TPSD images with Software for CSPos-Spos. FIG. 9: "Median Plans of the Standard Model" (4):

9a: TX-SP Superior Transverse Plan; 9b: TX-IF Inferior Transverse Plan

9c: FY-AN Anterior Frontal Plan; 9d: FY-PO Posterior Frontal Plan;

9e: SZ-SI Left Lateral Sagittal Plan; 9f: SZ-DE Right Lateral Sagittal Plan;

Circles and squares symbolize the limits of Internal 1W and External 2W.

FIG. 10: "Chromatic Bands on Median Plans" for measures applied to a Person (26).

FIG. 10a: "The Chromatic Bands on the Transverse Plan (TX)" are arranged with 2 Chromatic Scales, one Leftward −X (Blue) and one Rightward +X (Green), to respect the standard sequence from 4 Blue Left to 7 Green Right, both for the left half and the right half.

FIG. 10b: "The Chromatic Bands on the Frontal Plan (FY)" are arranged with 2 Chromatic Scales, one Upward −Y (Azure) and one Downward +Y (Orange), to respect the standard sequence from 3 Azure Up to 8 Orange Down, both for the upper half and the lower half.

FIG. 10c: "The Chromatic Bands on the Sagittal Plan (SZ)" are arranged with 2 Chromatic Scales, one Backward +Z (Brown) and one Forward −Z (Violet), to respect the standard sequence from 2 Brown Back to 6 Violet Forward, both for the back half and ahead half.

FIG. 10d: "The Chromatic Bands on the Oblique Plan (OW)" are arranged with 2 Chromatic Scales, both graduated from Inward (Red) to Outward (Yellow), to respect the standard sequence from 1 Red Internal to 5 Yellow External.

FIG. 10e: "The Chromatic Bands are sized on the Silhouette of Person". Person measured in distension.

FIG. 10f: "Silhouette of Person" has performed a variation detected on the FY Chromatic Band.

FIG. 11a: "Photogram of tennis court" (33) in perspective with application of the Transverse Plan TX of the Standard Model (dashed lines) to the playing field (white lines).

FIG. 11b: "Construction of the tennis court in real sizes within the 4D program" (34). The superior half of the inner and outer spherical cubic Container is visible. Detection of Coordinates on the Transverse Plan, with respect to the center of the Model:

FIG. 11c: "Application of the Standard Model on Person" (35, FIG. 10ef). On the Y and Z Coordinates, 5 PESDs are detected FIG. 11d: "Photogram inserted in 4D Standard Model scaled on breadth of the Person" (36) for the detection of Coordinates with respect to the Orthogonal Plan chosen.

FIG. 11e: "Projection on the Orthogonal Plan of a PESD positioned in Photogram" (37) for the measurement detection with respect to the center of the Standard Model.

Figure 12A:
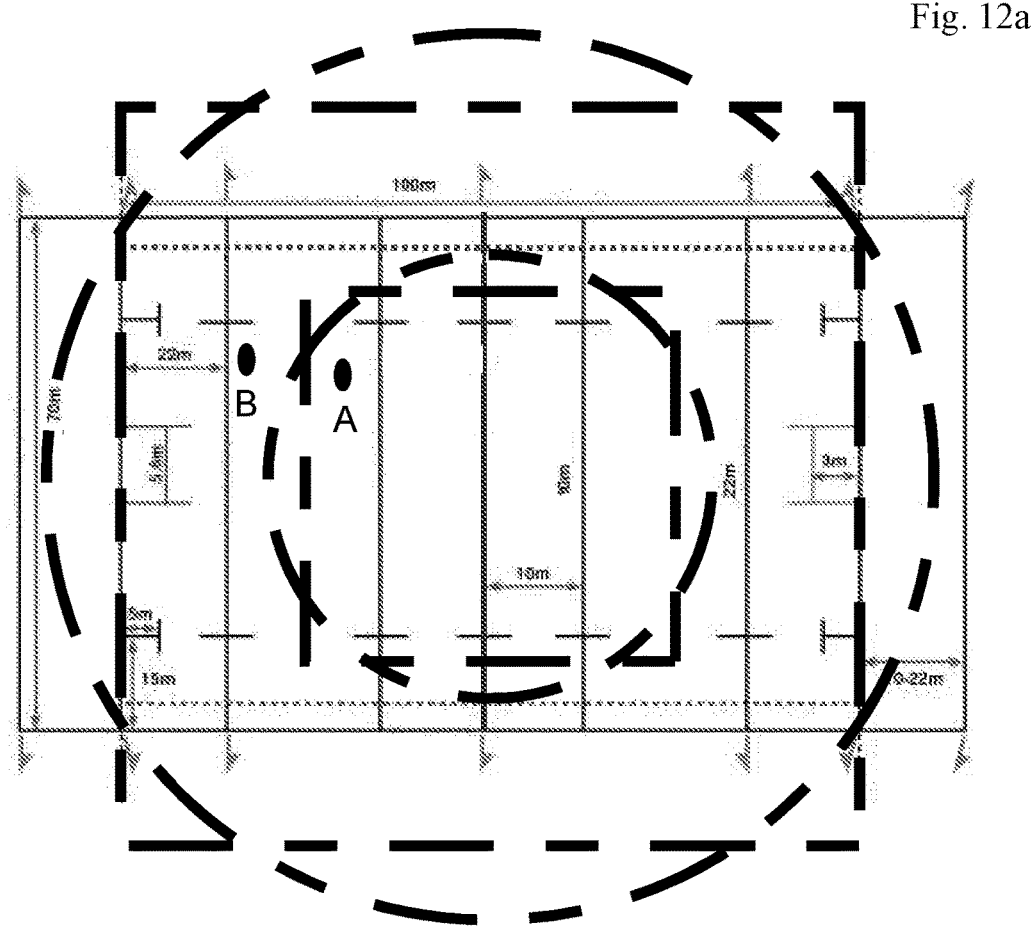
FIG. 12a shows an application of the container of the invention to a Rugby Sport Field.

FIG. 12a: "Rugby Sport Field". Standard Container, sized Cube Side 100 meters and Sphere Diameter 120 meters, can contain large environments, like a Rugby field. The Standard Model (dashed lines) is applied in reference to the support plan and displacement of the players.

A and B are positions of the Player silhouette on the Transverse Plan TX, on which the Superior and Inferior Grids and Combined Dimensions (FIG. 8a, 8b) coincide.

Figure 12B:
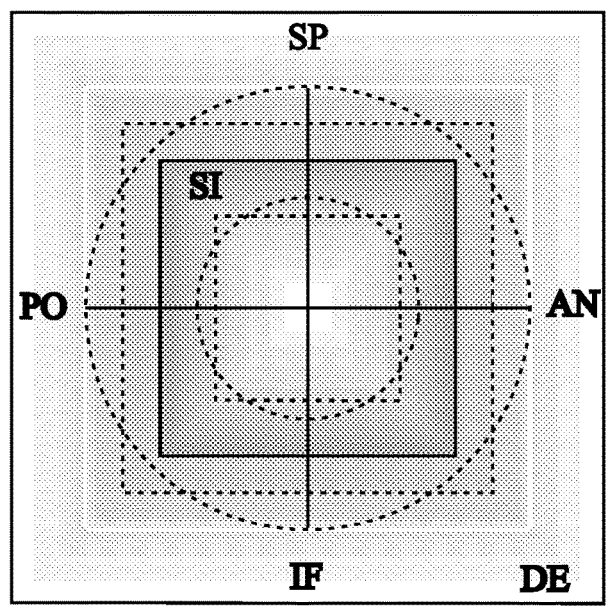
FIG. 12b shows an application of the container of the invention to a Hall.

FIG. 12b: "The Hall" with shaded walls is sufficiently large (continuous lines) to insert a Container m 10 Cube Side and m 12 Sphere Diameter.

The measurement Hall is oriented as Standard Model: AN, PO, SP, IF, DE, SI, Internal Cube Sphere and External Cube Sphere (dashed lines)

Figure 12C:
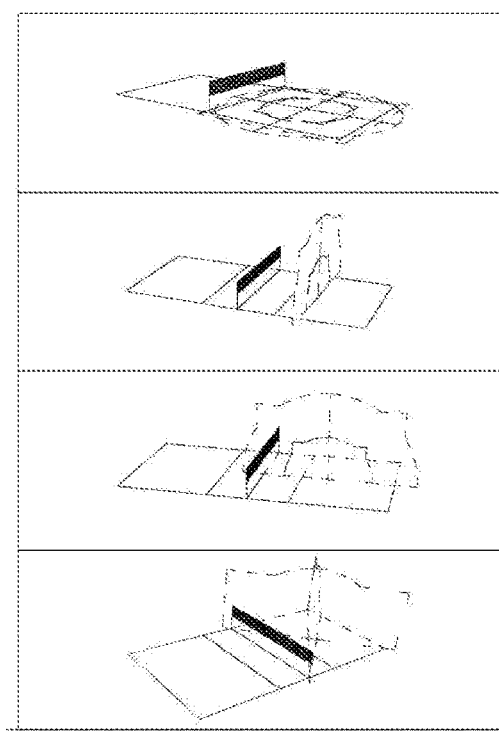
FIG. 12c: shows an application of the container to a Volleyball Sport Field with net.

FIG. 12c: "Volleyball Sport Field with net and applied Standard Model". Positions and displacements of the supports, that are PESDs of the players' silhouettes in contact with the ground, are detectable and measurable with reference to the Inferior TX Transverse Plan (FIG. 8b), coinciding with the floor level. The variations of the players' silhouettes, moving in the space, are detectable and measurable with the Superior Four-Dimensional Container: Superior Frontal Plan FY, Superior Sagittal Plan SZ, SuperiorOblique Plan OW.

Figure 13A:
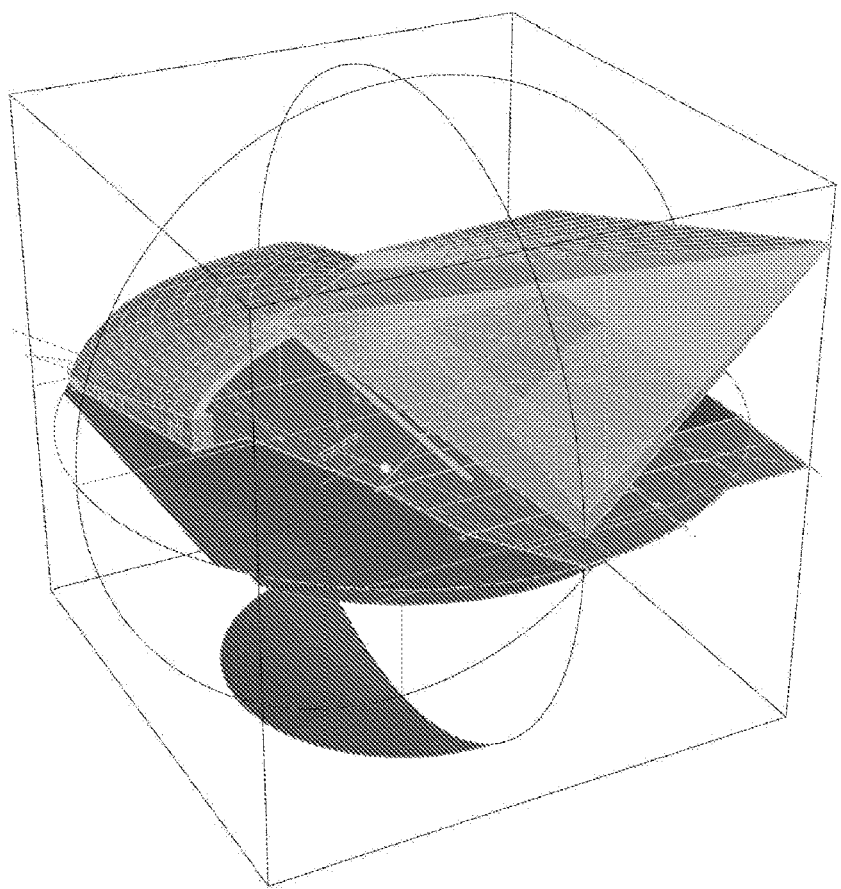
FIG. 13a shows an architectural space called Sfecumidoide organised as a TPSD Laboratory for the Study on Human Dynamics (SHD)

FIG. 13a: "Sfecumidoide TPSD Laboratory for the Study on Human Dynamics (SHD)". Margin lines of the Cubic Spherical Standard Container. Straight and curved surfaces defining the structure of the Laboratory such as floors, walls, equipment, spaces. Structure and equipment are mobile and adaptable to the activities.

Figure 13B:
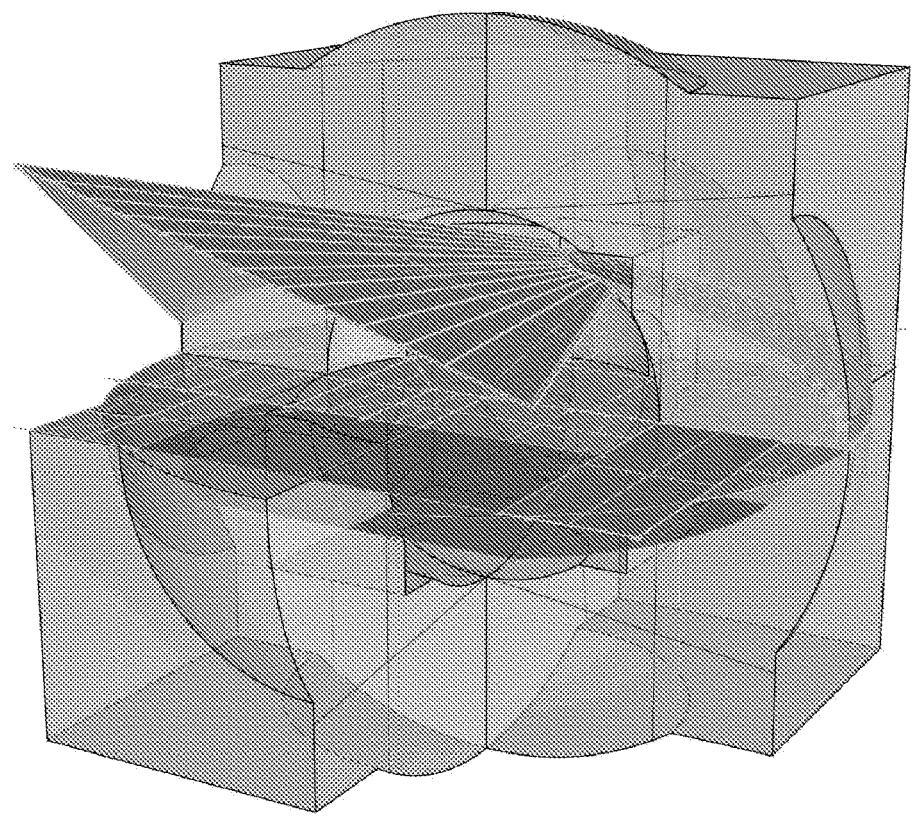
FIG. 13b shows a Sfecumidoide Prototype Container.

FIG. 13b "Sfecumidoide Prototype Container". Representation of the SHD Laboratory Prototype within the Cubic Spherical Standard Container. The definition structures, located in correspondence with the Simple and Combined Dimensions of the Standard Model, are visible.

With reference to the above described drawings, the following is a detailed description of embodiments of the present invention.

The description is made in the following 44 paragraphs:
(1) "Standard Model: Properties and Functions"
(2) "The measurement model is a Container"
(3) "The Simple Dimensions"
(4) "16 Combined Dimensions"
(5) "Position direction constrain".
(6) "The positive or negative Algebraic Signs"
(7) "Standard Cube Sphere Container"
(8) "With Four-dimensional X Y Z W reference system"
(9) "Standard Spheres and Cubes".
(10) "Standard Cube Sphere Ratios"
(11) "Example 1"

(12) "Example 2"
(13) "Example 3"
(14) "Example 4"
(15) "Example 5"
(16) "Example 6"
(17) "Example 7"
(18) "Dimensions of Personality"
(19) "Abstract Standard Container (CSAstr)"
(20) "Standard PESDs"
(21) "TPSD Software CSAstr"
(22) "Flow Chart of Symbology and Vocabolary"
(23) "Flow Chart Structure of Work Book"
(24) "Data processing procedure"
(25) "Cubic Spherical Standard Container for Position-Displacement applied to Person"
(26) "The Chromatic Bands system"
(27) "Example: the sizes of Silhouette of Person"
(28) "Variation of position"
(29) "Environments for Measurement CSPos-Spos"
(30) "Instrumental Technical Implant for Image Management"
(31) "Flow Chart: Photograms Treatment"
(32) "Photograms"
(33) "Photogram of tennis court"
(34) "Construction of the tennis court in real sizes within the 4D program"
(35) "Application of the Standard Model on Person"
(36) "Photogram inserted in 4D Standard Model scaled on magnitudes of the Person"
(37) "Projection on the Orthogonal Plan of a PESD positioned in Photogram"
(38) "Related Dimensions physical psychic Personality"
(39) "Hall and Sport Fields"
(40) "Sfecumidoide Prototype Container for Static Dynamic Personality Test"
(41) "Surface volume"
(42) "Standard Container for Scientific Categories"
(43) "Scientific theme categories"
(44) "TPSD Categories"
(45) "Electric measure category"

(1) "Standard Model: Properties and Functions"

Container Prototype Sfecumidoide (2); Originated from the Body Scheme of Human Being (6); Originated from the Human Psychophysical System (6); 8 Simple Dimensions of Position and Direction (3); 16 Combined Dimensions in constrained Position Direction (4); Balancing Chromatic Volumes (5); Quality of Chromatic Dimensions (43); Cubic-Spherical Dominances of Volumes and Lines (FIG. 2); Cube-Sphere Concentric Position Ratio (9); Cube-Sphere Correspondence Ratio (10); Scientific Categories (42); Four-Dimensional Grid (9); Scales with Unit of Decimal Measure (9); X Y Z W Coordinates of Points (41); Unit Points of Cubic-Spherical Volume (10); Gemini Points of Cubic-Spherical Volume (FIG. 3e); Static Dynamic Equilibrium Points (PESD) (8); Objective Measurement System (39); Comparative Reference System (39); Abstract Evaluative Analytical System (19); Position Displacement Evaluative Analytical System (29); Psychophysical Analysis and Evaluation System (18); Control System on Statics Dynamics Variations (28); Reference System for application of measures is organized in relation to a fixed structure (5).

(2) "The measurement Standard Model is a Container" (FIG. 3a). Dimensions or Volumes, within which subjects/objects/abstractions are measured, are used as a Prototype Container.

(3) "The Simple Dimensions" are (FIG. 2): Lateral Rightward (+X), Lateral Leftward (−X), Inferior Downward (+Y), Superior Upward (−Y), Posterior Backward (+Z), Anterior Forward (−Z), Intense Inward (1W), Extense Outward (2W). A Color is assigned to each of the 8 Simple Dimensions. Thus, the reference system is Four-Dimensional and Chromatic, with use of opposite Volumes.

(4) "16 Combined Dimensions". Each Simple Dimension is combined with the others to establish a reference system with 16 Combined Dimensions. Each Combined Dimension is collocated in an unique fixed site in the Container and constrained in a complete system of opposite Volumes (FIG. 1). To the Combined Dimensions, quality attributes and abstractions are referred, organized in a numbered 8 Colors system and White/Black and Density-Levels: 0 white, 1 red, 2 brown, 3 azure, 4 blue, 5 yellow, 6 violet, 7 green, 8 orange, 9 black (FIG. 2). The Positions and Directions Code of 16 Combined Dimensions is composed by Number associated with Dimension and Letter "i" for internal Combined Dimensions and Letter "e" for external Combined Dimensions. Each Chromatic Dimension represents appropriate themes and collects abstractions logically related, and related to the quality of the Colors (36).

(5) "Position direction constraint". The 16 Combined Dimensions (FIG. 1) in position-direction respect to Orthogonal Plans—Transverse Plan (TX), Frontal Plan (FY), Sagittal Plan (SZ)—are constrained with interlocking and represented by adjacent Volumes. Being used Oblique Axes Plans Spaces W, each Dimensions is represented with 2 opposite combinations of position-direction. The Model, logical and rational, is based on fixed ratios that confer to the system the quality of Standard for balanced measures. The constraint of combination and opposition give fundamental balance properties to the reference system. Each of the 16 Combined Dimensions, or Chromatic Volumes, are linked to 4 PositionsDirections (FIG. 2), or Four-Dimensional XYZW, with X on the Transverse Plan, with Y on the Frontal Plan, with Z on the Sagittal Plan, with W on the Oblique Plan.

(6) "The positive or negative Algebraic Signs" and orthogonal Positions Directions are determined with reference to the body system of the human being (27):
+X Psychophysical Dominance Lateral Rightward
−X Psychophysical Alternative Lateral Leftward
+Y Psychophysical Gravity Inferior Downward
−Y Psychophysical Antigravity Superior Upward
+Z Psychophysical Pressure Posterior Backward
−Z Psychophysical Advance Anterior Forward
1W Psychophysical In-Tension Intense Inward
2W Psychophysical Dis-Tension Extense Outward (7) "Standard Cube Sphere Container" (FIG. 2, 3a, 10b). The internal part of Container is delimited by 2 cubic-spherical edges at 1W value and the external part of Container is delimited by 2 cubic-spherical edges at 2W value. The Cubic-Spherical characteristics of Container are pointed out by Shape Volume Dominance in Combined Dimension Space and Shape Lines Dominance on the Combined Dimension Plan.

(8) "With Four-Dimensional X Y Z W reference system" (FIG. 3af), stability and variability of Static Dynamic Equilibrium Points (PESDs) are measured. The Standard Container is the reference system transferable to the various environmental contexts and fields of application. The Standard Container is made up of Cube Volume and Sphere Volume, to perform rectilinear and curvilinear measurements.

(9) "Standard Spheres and Cubes". The Container, crossed by the Four-Dimensional Grid (FIG. 3f) with XYZW Decimal Scales, has a number of Standard Spheres and Cubes (FIG. 3b) coinciding with the Coefficients, in the integer Value and second order, tenth and hundredth value.

Of a Container with cube edge 100 Values and sphere diameter 120 Values:
- at the integer value there are 50 Standard Cubes and 50 Standard Spheres
- at the decimal value there are 500 Standard Cubes and 500 Standard Spheres
- at the centesimal value there are 5000 Standard Cubes and 5000 Standard Spheres.

The stability, of corresponding Standard Spheres and Cubes, determines measurements on 4 relatable X Y Z W Coordinates. Cubes and Spheres are concentric, intersected, corresponding, in a Proportion Ratio at the Value 5 Half-edge Cube and at the Value 6 Radius Sphere (FIG. 3b). Consequently, the measurement applications are related to a regular and balanced structure. If the Cube were tangent to the inner or outer Sphere, with different ratios, it would be either too big or too small.

(10) "Standard Cube Sphere Ratios":
Concentric Position Ratio
Proportion Ratio 5 Half-edge Cube and 6 Radius Sphere
Intersection Ratio
Equivalence Ratio
Constance of Distances For Standard Model measures, the ratios are constant. Measurements are executed using Unit Points (PU) of Grid, Gemini Points (PG) of Correspondence, Static Dynamic Equilibrium Points (PESD) of variation. For Constancy of Distances, in the Cube Sphere reference system, necessary regularities are stabilized for the measurement applications (FIG. 3c). For Equivalence Ratio, for each Point placed on the Cube, there is a corresponding Point on the Sphere, and vice versa (FIG. 3b). The spherical cubic equivalence ratio allows measurements of corresponding rectilinear and curvilinear dynamics with reference to the Median or Oblique Plans (FIG. 10).

(11) "Example 1" (FIG. 3a). The 25th Standard Sphere, which divides the Internal Container from the External Container, has the coefficient Value 30 on the Median Orthogonal Plans, so that, applying the 1/6 subtracted proportion (10), as the rule stabilizes, the corresponding Standard Cube coincides with the coefficient Value 25 on the Orthogonal Median Plans of the 25th Standard Cube.

(12) "Example 2" (FIG. 3b). Cubes and Spheres are concentric and of proportional size, so that at Value 5 half-edge corresponds the Value 6 radius on the Orthogonal Median Plans. To make comparable rectilinear and curvilinear dynamic measurements, the Points in equivalence ratio are used, one cubic and one spherical corresponding, To each spherical measure corresponds a cubic measure and vice versa. A cubic PESD has X Y Z Coordinates Values 1/6 less than the X Y Z Coordinates Values of a spherical PESD. A spherical PESD has X Y Z Coordinates Values 1/5 more than the X Y Z Coordinates Values of a cubic PESD. The constancy of the proportions allows a confrontation between comparable measures. With Four-dimensional Grid, Cubic PESD +1X +1Y +1Z 1.73W Coordinates has a corresponding spherical PESD +1.2X +1.2Y +1.2Z 1.2W Coordinates.

(13) "Example 3" (FIG. 3c). "Constance of Distances", segments or lengths, is a fundamental property of the standard measure system. Segment M is equal in length to segment L (thick lines), because the rectilinear distance and curved distance ratio is calculated at the minimum of equivalence. On the perimeters of the corresponding square and circular sections, proportion ratios are stabilized.

The straight segment, between two squares, is repeated 24 times on the perimeter of the square section. The curved segment, comprised between two circles, is repeated 16 times on the perimeter of the circular section.

(14) "Example 4" (FIG. 3d). PESDs, cubic and spherical, have identical absolute coefficients. Given the PESD in Dimension 5ee Dark Yellow Outward Backward Rightward Upward, Coordinates +12X −23Y +19Z 32W the Standard Sphere is identified, as the 27th, finding the corresponding Standard Cube, that is the 27th, numbered as the Value 27 (rounding to the integer value) of the Orthogonal Coordinates, that is 32 of radius minus 1/6 of the radius. Given the PESD in Dimension 8i Dark Orange Inward Backward Leftward Downward, −12X +23Y +19Z 32W Coordinates, the Standard Cube is identified, as the 23th, detected on the Cube having the size of the largest Orthogonal Coordinate, in the case +23Y, which also contains the X Z Coordinate Values.

(15) "Example 5" (FIG. 3fg). PESD displacement in a Standard Four-dimensioned Container with real measures of Cube's quarter at the values m 2.00 X 2.00 Y 2.00 Z 3.5 W. Visible 3 cube faces and 3 sphere cups. PESD A with Coordinates −1.50 X −1.20 Y −0.40 Z 1.96 W is in Light Azure volume 3e spherical dominance. PESD A moves to the next position of PESD B with Coordinates −1.70 X −1.60 Y −0.20 Z 2.42 W; curvilinear displacement lasts up to it remains in the spherical dimension. PESD C with Coordinates −1.80 X −1.60 Y 0 Z 2.41 W and the subsequent PESD D with Coordinates −1.80 X −1.60 Y +1.40 Z 2.40 W are Light Brown 2e cubic dominance and trace a detectable variation on rectilinear dominance. For standard ratios, A B C D tracings are broken down either as rectilinear or curvilinear (FIG. 3g).

(16) "Example 6" (FIG. 3e). The Gemini Points, one cubic and one spherical, in the cubic spherical volume, correspond on the Oblique Axis W. PESDs move, within the Standard Cube Sphere Container, in straight line or in curved line. With a PESD in curvilinear displacement, which is Spherical PESD A, Values +18X −26Y −33Z Coordinates are detected. The Spherical PESD A has the Radius of the Value W that is Polar Coordinate 45.70 of 3808th Standard Sphere (9). The Gemini Cubic PESD B stands on the 3808th Standard Cube and on the Diagonal passing from the Center and the Spherical PESD A. With Four-Dimensional Grid is detected the point of intersection that is the Cubic PESD B +20.77X −30.01Y −38.08Z 52.75W Coordinates.

With PESD in rectilinear displacement, which is Cubic PESD A, Values +18X −26 Y −33Z Coordinates are detected. Cubic PESDA has the Polar Coordinate 45.70 as W. The Standard Cube containing the PESD is the one passing from the Coordinate to the highest value −33Z. The Standard Cube is the 33° and the corresponding Standard Sphere is the 33°. With Half edge Value 33, the Radius is proportionally 39.6 Value. The corresponding Gemini Spherical PESD C is on the Standard Sphere 33° at the intersection with the Diagonal passing from the Center and the Cubic PESD A. With Four-Dimensional Grid is detected the corresponding Spherical Point C that has +15.6 X −22.53 Y −28.6 Z 39.6 W Coordinates. With identical spherical PESD and Cubic PESD coefficients, the Standard Sphere Cube, to which reference is made, is chosen according to the original dynamics of the displacement detected, or in curvilinear or in rectilinear.

(17) "Example 7" (FIG. 3c). Using the Standard Proportion of the straight segment P and the corresponding curved segment N, there are 3 Spherical PESD N1, N2, N3 corresponding to 1 Cubic PESD P1. Thus, the straight segment P1P2 has as correspondents: a Minimum curved segment N3N4, a Medium curved segment N2N5, a Maximum curved segment N1N6. The minimum medium maximum correspondence is used to relate distances in a constant way. A rectilinear displacement in measuring is related to the minimum medium maximum curvilinear distances. The correspondence of curvilinear and rectilinear segments is movable, when necessary.

(18) "Dimensions of Personality" are typical tendencies of the observed Person subject, sought in physical psychic scope. They emerge from data analysis and processing (FIG. 7,11), on static and dynamic points. On Static Dynamic Equilibrium Points (PESD) the Personality frame is composed. The Abstract Standard Container (CSAstr) is used for conceptual cognitive components. The Position Displacement Standard Container (CSPos-Spos) is used for analysis of movement.

(19) "Abstract Standard Container (CSAstr)". CSAstr is applied to conceptual cognitive scope, to carry out analysis and qualitative description of Person subject. Reproduced as a virtual model in TPSD Software, it constitutes the measure reference system. The TPSD Software, supporting the Static Dynamic Personality Test (TPSD), uses the Abstract Geometric Plan of Standard Model (FIG. 4a). Standard Tables support analysis and interpretation of Personality (24). The TPSD Software translates into standard data the information, produced by an Applicant, passing through a calculation system and standard tables. With TPSD calculations and abstract evaluations are elaborated, referring to the psychodynamic scope.

Meaningful Items, organized in Scientific Categories (44) based on the Standard Model, support the interpretation of Personality. Standards Static Dynamic Equilibrium Points are integrated into algorithmic procedures (FIG. 4b). The standard model PESDs are the reference structures for analysing and interpreting the spatial, cognitive and conceptual components of Personality.

(20) "Standard PESDs". On Abstract Geometric Plan (FIG. 4a), 80 Standard PESDs are identified on straight lines of squares and on curved lines of circles (FIG. 4b). Each Standard PESD is assigned: Combined Dimension, Color, X Y Z W Coordinates, Scientific Category Item, Area, Volume. 5 Standard PESDs are fixed on each Combined Dimension. Standard PESDs are defined by Original Coordinates X Y and Derived Coordinates Z W.

(21) "TPSD Software CSAstr". TPSD Software is automated with macros that preside over the processing of main calculations and facilitate the operator in the selection and processes of preparation/performance. Algorithmic process automation is represented by Flow Charts:

Step 0 Preliminary preparation of Test Sheets; Step 1 Compilation and processing of Cross Points; Step 2 Determination of PESD-T and PESD-A; Step 3 Calculation of PESD-T Chromatic Area: Step 4 Interpretation;

Flow Chart of Symbology and Vocabulary (FIG. 6);

Flow Chart of Work Book Structure (FIG. 5).

(22) "Flow Chart of Symbology and Vocabulary" (FIG. 6). Description of types of Blocks and their functions:
1 Start-End procedure Block;
2 Iteration Block for repeated procedures;
3 Dichotomic Choice Block between different opportunities;
4 Automatic Processing Block performed by software;
5 Processing Block with Operator Intervention;
6 Data Block and alternative Results;
7 Processing Manual Block or external to Book Excel TPSD;

Legend Abbreviations and Vocables

(23) "Flow Chart: Structure of Work Book" (FIG. 5). Work-Book structure explains the layout of Spreadsheets and their functions:

"Flow Chart Step 0". Procedural scheme of preparation Spreadsheets of Affirmants/Themants Sheets and of Main Sheet.

"Flow Chart Step 1". Compilation and processing of Cross Points (CR Points), produced in the definition step of standard data from raw data.

"Flow Chart Step 2". Determination of PESD-T and PESD-A, with attribution of color and position-direction on standard graph.

"Flow Chart Step 3". Calculation of PESD-T chromatic Area, between PESD-T PESD-A PESD-Central, to define Personality Dimension.

"Flow Chart Step 4". Interpretation extracted from Software functions and observation and analysis phases for personality assessment.

(24) "Data processing procedure", activated by: "Default" to enable the Software procedure; "N Affirmants" which can be activated with the "Standard List"; "Delete List" to cancel titles and activate new Affirmants, as an alternative to Standards; "Prepare Sheets" to activate Electronic Affirmants Sheets; in "Tables Parameters", information about the Standard Table Sheet is stored; in "Main Parameters", information from the Main Calculation Sheet is indicated (FIG. 7); "Affirmant Electronic Sheets" with "Crosses Schema" 5 Themants "0 1 2 3 4" and "Item Cards"; "Primary and Rotated PESDs Mask" with Coefficients and Chromatic Dimensions of Standard PESDs; "Graphic Mask" 16 Combined Dimensions 8 Sectors 4 Levels with Averages calculation; "Level Colors Table Mask" with buttons that activate the PESD Chromatic Dimension; "Category Mask" to insert link between Item and Color, defined by Category"; "Item Themant Sheet" and "Interpretation Sheet" with data and descriptions on Personality Dimensions; "Straight-Lines and Points Spreadsheet" to find margins of PESD Chromatic Dimension; "Area/Volume Calculation Spreadsheet" to quantize Chromatic Dimension of PESD.

(25) "Cube-Sphere Standard Container for Position-Displacement (CSPos-Spos) applied to Person".

It measures stability and dynamic variations of Person with reference to 16 Combined Dimensions in 4D (FIG. 3f) and 8 Simple Dimensions in 2D (FIG. 10). The Standard Model, represented in a 2D scheme, is applicable to each image of Person using Geometric Plane Chromatic Bands with proportionally gradable Scales. Application of Standard Model to a Person is performed to carry out quantitative and qualitative measurements related to variations with respect to psychic-corporeal balance centers. Position and displacement of Person are broken down with reference to 8 Simple Dimensions. The Simple Dimensions are shown on the Median Plans and indicated by colors and numbers (FIG. 2).

(26) "The Chromatic Bands system" is composed of: TX Chromatic Bands, FY Chromatic Bands, SZ Chromatic Bands, OW Chromatic Bands (FIG. 10abcd). The 4-Scheme System of Chromatic Bands is sized on a Silhouette of Person and applied respecting the correspondence with Body Scheme (6), universally known in Right and Left Lateral, Superior and Inferior, Anterior and Posterior, Internal and External parts. Standard sequence of Chromatic Bands: 0 White, 1 Red, 2 Brown, 3 Azure, 4 Blue, 5 Yellow, 6 Violet, 7 Green, 8 Orange, 9 Black. Chromatic Bands system center coincides with the Silhouette of Person equilibrium center identified on navel; it is used to analyze position of parts or entire body.

(27) "Example: the sizes of Silhouette of Person", in a stretched out position, are (FIG. 10e):

Dm 23.76 distance of stretched out body from phalanx of feet to phalanx of hands;
   dm 10.00 feet heel and navel distance; dm 7.00 apex head and navel distance;
   dm 12.60 high hands phalanx and navel distance;
   dm 5.00 shoulders extremes distance;
   dm3.00×2.00 neck head oval extremes distance.

The heels of the feet are coincident to the limit of Downward Orange Cubic Dimension, representative of a support plane. Analysis of position is performed to evaluate margins, sizes, proportions, ratios, with reference to Chromatic Dimensions and appropriate Scientific Categories.

(28) "Variation of position" (FIG. 10f). The X Y Z W Coordinates are measured as in example of Y Coordinate of navel Silhouette of Person and variation of position. Range sized on Silhouette of Person, stretched out body with maximum position amplitude (FIG. 10e) and extreme bands White/Black, divided into 10 parts as the number of Simple Dimensions and Black White:

on FY: +Y=dm13.20; −Y=dm13.20; on TX: +X=dm13.20; −X=dm13.20. Each dimensional tenth is dm1.32. PESD navel in Dimension 3 Azure Yom=dm3.58 downward (+Y) with respect to Y=dm0 of navel in initial position (FIG. 10ef).

(29) "Environments for Measurement (CSPos-Spos)". An Instrumental Technical Implant is installed in environments as a Hall or a Sport Field, where the activities take place (FIG. 11,12). Hall or Sports Field and Person subject are visible by means of video-cameras or photo-cameras, from the Right or Left Lateral, Superior or Inferior, Posterior or Anterior views. The Standard Container, applied to Hall or Sports Field, is the reference system in which position and displacement measurements (CSPos-Spos) of Person subject are detected. The X Y Z Scales, with integer, first and second decimal values are included on rulers or grids applied to Hall or Sports Field in 2D and 3D; W Scale is applied on 4D screen.

The dimensional coincidence on the screen, between External Internal Standard Container and Hall or Sports Field with rulers or grids, allows detecting PESD positions of a dynamic Person subject with respect to the environment, in representation on the photograms.

(30) "Instrumental Technical Implant for Image Management".
   IP wireless cameras or video-cameras or photo-cameras, network transmission;
   Video-cameras or photo-cameras Synchronization System;
   Standard Computer and Screen;
   Contemporary visual tracking, simultaneous recording from Video-cameras or Photo-cameras;
   Tracking for subjects without markers by TPSD Software for static dynamic analysis: slow motion programs, 2D 3D 4D programs for selection and sizing of photograms and image measurement, programs for analysis and processing of lexical geometric mathematical data.

Technical Instrumental Implant for managing images on photograms, installed in the Room or at the Sports Field, works as a data detector, information processor, results transmitter.

Fix the cameras with synchronization system with respect to Hall or Sport Field for central views from right and/or left, from back and/or front, from below and/or above
   Start the synchronized cameras and keep the recording in video or in continuous shooting photos for the duration of the dynamic action
   Select in slow motion the synchronized photograms of the dynamic action
   Dimension the photograms automatically in reference to the sizes of the real environment (Hall, Sport Field) coinciding (FIG. 11) with the Standard Cube Sphere Container (2D 3D and 4D TPSD programs)
     Insert the dimensioned photograms in the virtual environment of Standard Container and position them in correspondence with the X Y Z W Plans
     Detect the PESD Coordinates, Static Dynamic Equilibrium Points chosen in measurement, with reference to the Median Plans of the Standard Container and identify the Simple and/or Combined Chromatic Dimensions of PESD
     Elaborate the quantitative and qualitative data identifying and explaining the distances between PESDs, variations of times and PESDs positions, PESD areas and volumes (24), scientific or thematic categories of PESD (42)
     Interpretation of the data extracted from the TPSD CSAstr Software and from the photogram treatment sequence with use of Software for CSPos-Spos TPSD, obtaining the description of the Static Dynamic Personality Dimensions of a Person subject.

(32) "Photograms" (FIG. 11). The photograms, extracted from the sequence recorded with cameras, are treated as data that inform about positions and variations of the silhouette of the person with respect to their center of body balance and with respect to the sports field. Being a system of analytical detection of dynamics without the use of markers, the Static Dynamic Equilibrium Points are indicated on the photograms as reference points for the measurement, and related to the Standard Model.

(33) "Photogram of tennis court" (FIG. 11a) in perspective with application Transverse Plan TX Standard Model to the playing field for measuring displacements with respect to the ground

(34) "Construction of the tennis court in real sizes within the 4D program" (FIG. 11b). The photogram, with the silhouette of the tennis player in vollèe lunge (FIG. 11c), is positioned and sized automatically on the lens point and compared to the tennis court with Standard Model 4D applied. The Superior half of the inner and outer Spherical Cubic Container is visible. Detection of Coordinates on the Transverse Plan, with respect to the center of the Model:

1) tip of the left foot has Anterior Forward Coordinate −Z=dm45.54 and Lateral Rightward Coordinate +X=dm18.48 Dimension 8e Light Orange Downward Rightward Forward Outward. Distance W dm49.15.

2) tip of the right foot has Anterior Forward Coordinate −Z=dm25.99 and Lateral Rightward Coordinate +X=dm12.18 Dimension 1ii Light Red Inward Downward Forward Rightward. Distance W dm28.71.

(35) "Application of the Standard Model on Person" (FIG. 11c). On the photogram is applied the Sagittal Plan Standard Model with Scales for Posterior Anterior and Inferior Superior measurements. The extremes are referred to as PESD or reference points for measurements. On the Y and Z Scales, 5 PESDs are detected that measure the position of the extremes with respect to the equilibrium center of the tennis player body: Vertex Head −Y=dm6.76, −Z=dm1.92; Right Hand +Y=dm2.03, −Z=dm8.19; Buttocks +Y=dm0.22, +Z=dm1.97; Left Knee +Y=dm0.42, −Z=dm4.25; Right Foot +Y=dm5.60, +Z=dm9.50; Left Foot +Y=dm6.47, −Z=dm6.62. The data are then related to other data extracted from the synchronic photograms on the Frontal and Transverse Plans.

(36) "Photogram inserted in 4D Standard Model scaled on sizes of the Person" (FIG. 11d) for the detection of Coordinates with respect to the selected Orthogonal Plans. Standard Model TX is applied for photogram with view from above or below; Standard Model SZ is applied for photogram with view from the right or left side, Standard Model FY is applied for photogram of view from front or back.

(37) "Projection on the Orthogonal Plan of a PESD positioned in Photogram" (FIG. 11) for the measurement detection with respect to the center of the Standard Model applied to the sports field. The PESD in projection is measured with respect to the Standard Model Scales and positioned with respect to the Combined Dimensions (FIG. 1)

(38) "Related Dimensions of physical psychic Personality". The Personality Dimensions extracted with the use of the CSPos-Spos Instrumental Technical Implant are related to the Dimensions extracted from TPSD Software CSAstr. Being a single Standard Model applied to Personality, both physical and psychic, there are multiple correlations to explain the dimensional links: Standard PESD positions and PESD Person, Affirmant Items and Category Items associated with subject Person, quantity/quality Coordinates Areas Volumes, directional tendency. In the tennis player example, from "Main Sheet" the Blue Dimension is highlighted in greater breadth with reference to the data collected from the analysis of the dynamics in the tennis field and in particular to the execution of the technical fundamentals, complete and well trained (FIG. 7,11).

(39) "Hall and Sport Fields" (FIG. 11). Stability of the system with Standard Model allows to carry out objective and comparable measurements. Standard Model is applicable to environments with diverse shapes and sizes. Shapes and sizes of Hall and Sport Field can be transferred in the virtual Cubic Spherical Standard Container. Positions and displacements of silhouettes of Person or Player are detectable as PESD measured within the Container.

(40) "Sfecumidoide Prototype Container for Static Dynamic Personality Test" (FIG. 12ab). The name Sfecumidoide is an acronym composed of: SFE of sphere, CU of cube, MID of pyramid, OIDE of ovoid. Prototype Container, with Cube edge 100 meters and Sphere Diameter 120 meters, is a real scientific Laboratory for the Study of Human Dynamics (SHD) with TPSD measurement systems. The structures of the SHD Laboratory are developed within the margins of the Standard Container: flat and curved walls, pyramidal roof, square and circular floor, water and ground spaces under the floor level. Structures and equipment of the Sfecumidoide Laboratory are modeled and flexible, adapted to the Simple-Combined Standard Dimensions and suitable for static dynamic activities in quantitative and qualitative measurement by Software TPSD CSAstr and ITS CSPos-Spos. In relation to the Standard Dimensions, defined by the Scientific and Thematic Categories, the modeling of the real environment is designed in accordance with the dynamics in measurement: each Standard Dimension accepts activities in relation to CSAstr and CSPos-Spos.

Example: water space located in Dimension 4e Light Blue Leftward Downward Backward Outward, with equipment suitable for natatorial activities performed by People subjects.

(41) "Surface volume". The data extracted from measurements inform about the dynamic tendency of individuals or groups, within a selected reference system to detect stability and variations in surface volume.

Surface volume is selected within the ranges (L cube edge, D sphere diameter, m meters):
Transverse Plan −X<m 100L 120D>+X
Frontal Plan −Y<m10L 12D>+Y Sagittal
Plan −Z<m100L 120D+Z Oblique Plan m 0<W>m 100
To quantify the measure, use (CSPos-Spos):
PESD detection from the Median Plans
PESD detections from Four-Dimensional Grid with Scales
To qualify the measure, use (CSAstr):
PESD detections on the 16 Chromatic Dimensions—
Scientific Categories for abstract evaluation
From the Median Plans of the Standard Model (FIG. 9, abcdef), PESDs are detected, positioned or moving within the entire selected volume.
From the Median Plans TX FY SZ, intersected at the value 0, the distances of PESD are detected.
Polar Coordinate coefficient W measures the distance from environmental center. Coefficient W calculated with average X Y Z measures the average distance from environmental Median Plans.
The surface volume is prearranged for the evaluation of displacements, detected as sequential positions located in the spaces, in reference to Grids and Combined Dimensions.

(42) "Standard Container for Scientific Categories".

On the Standard Model, "Categories" are structured and defined. The Standard is conceptually categorized to qualify and explain events of statics and dynamics. The Scientific Category is the conceptual stability structure necessary to evaluate the quality of the PESD and to order the abstract and logical elements. Each Scientific Category consists of 10 Thematic Categories, each consisting of 10 Items corresponding to the 8 Chromatic Dimensions and White/Black. The Category is the analytical and logical abstract reference system, organized into groupings of concepts, represented by meaningful Items and corresponding Chromatic Dimensions. Each Chromatic Dimension is represented by inherent themes, as in the following examples:

White: nativism, candid, milk, eyeball, water lily, preliminary or simply lack;
Red: blood, warm, love, danger, attention, nuclear or simply fire;
Brown: tanning, historicity, concreteness, fixity, trunk, structure or simply earth;
Azure: air, lightness, clarity, thought, philosophy or simply celestial sphere;
Blue: massive, complete, conceptual, mobility, fluidity or simply sea;
Yellow: elasticity, extension, exteriority, quality, rarity, preciousness or simply gold;
Violet: ultraviolet, scientific, advancement, intelligence, modernity or simply artifice;
Green: permissiveness, method, regularity, balance, biologic or simply nature;
Orange: particular, party, compound, chemistry, or simply dry leaf;
Black: armaments, war, darkness, mourning or simply blackberry.

The abstract contents, or ordered meaningful Items, are logically and contextually connected to the PESD element under evaluation, represented in the model, both in CSAstr and in CSPos-Spos. The measurement of the physical structure of the element, or PESD, is carried out in accordance with the measure of the psychic structure of the same element analyzed and evaluated ( ).

(43) "Scientific theme categories" on purpose are constructed and inserted in TPSD Software, specific and survey-related. The Category has a title related to the topic. Each Dimension is represented by a meaningful Item and inserted in the categorical scheme, in combination with other Items representative of the other Dimensions. In a Scientific Category, whose the binding theme is transport vehicles, the Items describe the concepts; each concept corresponds to a Chromatic Dimension. Example: Scientific Category "Vehicles": (0White) Playing Vehicles—(1Red) Motor Vehicles—(2Brown) Rail Transportation—(3Azure) Aircrafts and Airplanes—(4Blue) Boats and Ships—(5Yellow) Rescue Vehicles—(6Violet) Astronautic Vehicles—(7Green) Animal-drawn Vehicles-(8Orange) Means of Transport—(9Black) War Vehicles.

Each Item can be subdivided into a more detailed Thematic Category.

Example: 3Azure Dimension of the "Vehicles" Scientific Category:

Thematic Category "Aircrafts and Airplanes":

(0White) Atmospheric Air: vehicle moving chemical elements and microorganisms (1 Red) Propelled Airplanes: vehicles with engine and fuel ignition (2Brown) Cargo Airplanes: heavy transport vehicles (3Azure) Gliders and Wind-Aircraft: vehicles transported by winds (4Blue) Hydrofoils: vehicles moving on the water (5Yellow) Helicopters and Relief Airplanes: emergency vehicles (6Violet) Space-crafts and Astronautic Airplanes: artificial scientific vehicles (7Green) Birds and Winged: vehicles of biological nature (8Orange) Parachutes, Airships, Hot Air Balloons: vehicles with instrumental utility (9Black) Missiles Warplanes: vehicles of death.

(44) "TPSD Categories" In the TPSD Software CSAstr (21) the Scientific Categories used and named in the Standard List are: Dynamic 0, E-Psyche 1, A-Physique 2, Human 3, Conscience 4, Luminous-Physics 5, Time-Space 6, Vegetal-Animal 7, Instrumental 8, Game 9.

The title of the Scientific Category is that of the Affirmative Sheet. The TPSD Software presents a sequence of Thematic Categories belonging to these broader Scientific Categories. The Item Words, which compose a Thematic Category, are written on the Mask Squares and Category of the Themant Items Pattern. These Item Words are then transcribed on the Affirmative Electronic Sheet in groups of 4 and arranged on the Themant Cross Pattern (Flow Charts). The extracted data are placed in a categorical relationship, necessary to carry out the interpretation and describe the Dimensions of Personality. Scientific Categories applied to the Abstract Standard Container are used in TPSD, for example in the interpretation of the personality with "Sentiments" Category:

(B) Bliss; (RO) Love; (MA) Ire; (AZ) Happiness; (BL) Calm; (GI) Confidence; (VI) Fear; (VE) Courage; (AR) Humility; (N) Sadness.

Each Item in Scientific Category is explained by the Thematic Category Items, in organized order for the detailed interpretation of the personality components: Cowardice (VE) and Terror (MA) are examples of sub-categorical Items of the Fear (VI).

(45) "Electric measure category". The categorical system of abstract organization can be used in physical or technological fields to explain ties and constrains between the various Category Items in a specific and complete order. Example: "Electric Measure" Category: (B) inductance Henry; (RO) electric potential Volt; (MA) resistance Ohm; (AZ) electric charge Coulomb; (BL) induction flow Weber; (GI) frequency Hertz; (VI) electrical capacity Farad; (VE) electric current Ampere; (AR) power Watt; (N) conductance Siemens.

This example is possibly applied in a specific case for the interpretation of scientist's personality.

The foregoing description exemplary embodiments and examples of the invention will so fully reveal the invention according to the conceptual point of view, so that others, by applying current knowledge, will be able to modify and/or adapt for various applications such embodiments without further research and without parting from the invention, and, accordingly, it is to be understood that such adaptations and modifications will have to be considered as equivalent to the specific embodiments. The means and the materials to put into practice the different functions described herein could have a different nature without, for this reason, departing from the field of the invention. It is to be understood that the phraseology or terminology that is employed herein is for the purpose of description and not of limitation.

The invention claimed is:

1. A method for the automatic execution of a Static Dynamic Personality Test (TPSD) of a person, said method being characterized by comprising the steps of:

prearrangement of a cubic-spherical container obtained by merging concentrically a cube and a sphere, wherein the ratio between half edge of the cube and the radius of the sphere is 5/6, in such a way that the cube and the sphere intersect each other;

providing a model algorithm comprising predetermined tables, said tables associating combinations of positions of said cubic-spherical container to predetermined test categories, wherein said combinations of positions are determined according to a set of three measurements in an orthogonal XYZ system with parallel directions to edges of said cube, and a fourth measurement W according to a radial direction from the center of said container;

carrying out on said cubic-spherical container steps selected among:

physical steps comprising:

taking images of the person, overlapping said cubic-spherical container to said images, and measuring static-dynamic positions of said person as depicted in said images with respect to said cubic spherical container, obtaining a plurality of quantitative and qualitative position-displacement measurements of physical Static Dynamic Equilibrium Points (PESDs) of said person, and then automatically correlating of said physical PESDs to said tables of said model algorithm, obtaining a physical Static Dynamic Personality Test result;

psychic steps comprising:

projecting said cubic-spherical container on a plane, obtaining a projected plane container, selecting by said person a plurality of psychic Static Dynamic Equilibrium Points (PESDs), and measuring the position of said psychic Static Dynamic Equilibrium Points (PESDs) with respect to said projected plane container, obtaining a plurality of quantitative and qualitative measurements of psychic Static Dynamic Equilibrium Points (PESDs) of said person, and then automatically correlating said psychic PESDs to said model algorithm, obtaining a psychic Static Dynamic Personality Test result;

a combination thereof obtaining a physical-psychic Static Dynamic Personality Test result.

2. The method according to claim 1, wherein said cubic-spherical container is a Position Displacement Standard Container (CSPos-Spos) that can be occupied both in position and in displacement by images of said person, or by said person physically or by parts of the body of said person, in a plurality of said PESDs and is configured as a cubic-spherical container with a cube side dimension between 1.00 dm-1000 dm, in particular between 1.00 dm-100.00 dm, and a sphere diameter dimension between 1.20 dm-1200 dm, in particular between 1.2 dm and 120.00 dm, said cube side dimension and sphere diameter dimension compared to real size of said person, of parts of the body of said person or of an environment in which said person is moving.

3. The method according to claim 1, wherein the said measurements are carried out in said cubic-spherical container comprise a set of three measurements in an orthogonal XYZ system with parallel directions to edges of said cube, and a fourth measurement W with a radial direction from the center.

4. The method according to claim 1, wherein the said steps of execution in said cubic-spherical container of a plurality of measurements and said steps of evaluation of said measurements according to said model algorithm are made by program means referred to said cubic-spherical container are carried out by an Instrumental Technical Plant configured for analysis, measurement, interpretation, evaluation of stability and dynamism of the personality, said Instrumental Technical Plant comprising a TPSD software that sets said Instrumental Technical Plant according to said cubic-spherical container.

5. The method according to claim 3, wherein
said cubic-spherical container has a center and said W Coordinate identifies the PESD with respect to a chromatic density which is maximum at said center and decreases as the distance from said center increases.

6. The method according to claim 5, wherein
said chromatic density that measures the W Coordinate of said PESD is identified according to an Intense-Medium Intense-Medium Extense-Extense Ordinal Scale and Interval Scale in intermediate degrees.

7. The method according to claim 6, wherein said W Coordinate, is calculated from an Inward Intense to an Outward Extense grade, by executing an Average of said X Y Z Coordinates responsive to a proximity of the PESD to predetermined Median Planes, TZ Transverse, FY Frontal, SZ Sagittal, and a W value is obtained by the resultant of distinct tendencies of each X Y and Z Coordinates to be more or less distant from a value 0 with respect to said Median Planes.

8. The method according to claim 1, wherein said PESD can be determined in a way selected among:

in a Spherical Volume dominance where the X Y Z Coordinates define, in quantity and quality, a position and direction in a curved mode, a definition step being provided of a Standard Sphere to which the PESD belongs, the said W Coordinate being calculated as the length of Standard Sphere Radius using the X Y Z Coordinates of the PESD identified in said Spherical Volume;

in a Cubic Volume dominance, wherein the X Y Z Coordinates define, in quantity and quality, a position and direction in straight mode, being foreseen a phase of definition of a Standard Cube to which the PESD belongs, the said W Coordinate being calculated as the length of the segment that joins the PESD to the Center;

in particular, if said PESD has a rectilinear trajectory said Cubic Volume dominance is selected, and if said PESD has a curved trajectory said Spherical Volume dominance is selected.

9. The method according to claim 8, wherein position-direction ratios and fixed proportion ratios of said PESD are calculated and delimited by concentric and intersected Volumes in Cubic Volume dominance and in Spherical Volume dominance and determined in proportion 5 for the cubic component with respect to half edge of the cube of said cubic spherical container and in proportion 6 for the spherical component with respect to the radius of the sphere of said cubic spherical container.

10. The method according to the claim 9, wherein said X Y Z W Coordinates are calculated on the base of the said Cubic Volumes and Spherical Volumes and measured with said proportion ratios, each PESD being represented as two correspondent points called Twin Points, one of cubic components and one of spherical components.

11. The method according to claim 8, wherein said components are measured according to Standard Cubes and Standard Spheres, according to which to a cube edge 100 and to a sphere diameter 120 the following respectively correspond:

to an integer value 50 Standard Cubes and 50 Standard Spheres to a decimal value 500 Standard Cubes and 500 Standard Spheres to a centesimal value 5000 Standard Cubes and 5000 Standard Spheres.

12. The method according to claim 1, wherein said step of automatically correlating said PESD to said model algorithm comprises an association of a predetermined color to a predetermined combination of position and direction.

13. The method according to claim 12, wherein in said association the following colors are
used according to the following list:

| SIMPLE POSITIONS-DIRECTIONS | SIGN - VALUE | COLOR | NUMBER |
| --- | --- | --- | --- |
| Lateral Rightward | positive algebraic sign +X | Green | 7 |
| Lateral Leftward | negative algebraic sign −X | Blue | 4 |
| Inferior Downward | positive algebraic sign +Y | Orange | 8 |
| Superior Upward | negative algebraic sign −Y | Azure | 3 |
| Posterior Backward | positive algebraic sign +Z | Brown | 2 |
| Anterior Forward | negative algebraic sign −Z | Violet | 6 |
| Intense Inward | 1W value | Red | 1 |
| Extense Outward | 2W value | Yellow | 5. |

14. The method according to claim 1, wherein in said association positive or negative Algebraic Signs and orthogonal Positions Directions of said components are determined with reference to the body system of the human being according to the following list:

+X Psychophysical Dominance Lateral Rightward
−X Psychophysical Alternative Lateral Leftward
+Y Psychophysical Gravity Inferior Downward −Y Psychophysical Antigravity Superior Upward +Z Psychophysical Pressure Posterior Backward −Z Psychophysical Advance Anterior Forward 1W Psychophysical In-Tension Intense Inward 2W Psychophysical Dis-Tension Extense Outward.

15. The method according to claim 12, wherein in said association the following combined dimensions are used according to the following list:

| Combined Dimensions | Cod. | Colore Code Color | Volume Dominance | Line Dominance |
|---|---|---|---|---|
| Outward Inward | 0 | White B Gray GB | | |
| Inward 1W (Simple) Backward +Z Upward −Y Leftward −X | 1i | Dark Red ROS Light Red ROC | Cubic | Rectilinear |
| Inward1W Forward −Z Downward +Y Rightward +X | 1ii | Dark Red ROS Light Red ROC | Cubic | Rectilinear |
| Backward +Z (Simple) Inward1W Downward +Y Rightward +X | 2i | Dark Brown MAS | Cubic | Rectilinear |
| Backward +Z Outward2W Upward −Y Leftward −X | 2e | Light Brown MAC | Cubic | Rectilinear |
| Downward +Y (Simple) Inward1W Backward +Z Leftward −X | 8i | Dark Orange ARS | Cubic | Rectilinear |
| Downward +Y Outward2W Forward −Z Rightward +X | 8e | Light Orange ARC | Cubic | Rectilinear |
| Rightward +X (Simple) Inward1W Forward −Z Upward −Y | 7 | Dark Green VES | Cubic | Rectilinear |
| Rightward +X Outward2W Backward +Z Downward +Y | 7e | Light Green VEC | Spherical | Curvilinear |
| Leftward −X (Simple) Inward1W Forward −Z Upward −Y | 4i | Dark Blue BLS | Spherical | Curvilinear |
| Leftward −X Outward2W Backward +Z Downward +Y | 4e | Light Blue BLC | Spherical | Curvilinear |
| Upward −Y (Simple) Inward1W Backward +Z Rightward +X | 3 | Dark Azure AZS | Spherical | Curvilinear |
| Upward −Y Outwadr2W Forward −Z Leftward −X | 3e | Light Azure AZC | Spherical | Curvilinear |
| Forward −Z (Simple) Inward1W Downward +Y Leftward −X | 6i | Dark Violet VIS | Spherical | Curvilinear |
| Forward −Z Outward2W Upward −Y Rightward +X | 6e | Light Violet VIC | Cubic | Rectilinear |
| Outward 2W (Simple) Forward −Z Downward +Y Leftward −X | 5e | Dark Yellow GIS Light Yellow GIC | Spherical | Curvilinear |
| Outward 2W Backward +Z Upward −Y Rightward +X | 5ee | Dark Yellow GIS Light Yellow GIC | Spherical | Curvilinear |
| Inward Outward | 9 | Black N Gray Black GN. | | |

16. The method according to claim 1, wherein said program means, or TPSD Software, assign to each combination of position-direction components qualitative aspects extracted by the cubic/spherical container are selected among: Dynamic, E-psyche, A-physique, Human, Conscience, Luminous-Physics, Time-Space, Vegetal-Animal, Instrumental, Game, and each qualitative aspects is defined as a respective Scientific Category, to each Scientific Category a sequence of Thematic Categories corresponding.

17. The method according to claim 1, wherein a physical cubical spherical container is further used that is configured as laboratory for the study of human dynamics (SHD) in which said TPSD measurements are carried out, said physical cubical spherical container having flat and curved walls, pyramidal roof, square and circular floor, water and ground spaces under the floor level, in such a way that static dynamic activities to which quantitative and qualitative measurements can be made.

\* \* \* \* \*

UNITED STATES PATENT AND TRADEMARK OFFICE
CERTIFICATE OF CORRECTION

| | | |
|---|---|---|
| PATENT NO. | : 11,786,157 B2 | Page 1 of 1 |
| APPLICATION NO. | : 17/266280 | |
| DATED | : October 17, 2023 | |
| INVENTOR(S) | : Claudia Gusso et al. | |

It is certified that error appears in the above-identified patent and that said Letters Patent is hereby corrected as shown below:

In the Claims

Column 25, Line 40, Claim 15, delete "7" and insert -- 7i --

Column 26, Line 32, Claim 15, delete "GN." and insert -- GN --

Signed and Sealed this
Second Day of January, 2024

Katherine Kelly Vidal
*Director of the United States Patent and Trademark Office*